United States Patent [19]
Isaacson et al.

[11] Patent Number: 5,211,546
[45] Date of Patent: May 18, 1993

[54] AXIAL FLOW BLOOD PUMP WITH HYDRODYNAMICALLY SUSPENDED ROTOR

[75] Inventors: Milton S. Isaacson, Dayton, Ohio; Anthony P. Lioi, Round Rock, Tex.

[73] Assignee: Nu-Tech Industries, Inc., Dayton, Ohio

[21] Appl. No.: 881,723

[22] Filed: May 11, 1992

Related U.S. Application Data

[63] Continuation-in-part of Ser. No. 529,598, May 29, 1990, Pat. No. 5,112,200.

[51] Int. Cl.⁵ .................................. F04B 17/00
[52] U.S. Cl. .................................. 417/356; 415/900; 604/151
[58] Field of Search ............... 417/354, 356; 415/900; 600/16; 623/3; 604/151

[56] References Cited

U.S. PATENT DOCUMENTS

| | | | |
|---|---|---|---|
| 3,143,972 | 8/1964 | Smith et al. | 417/356 |
| 3,433,163 | 3/1969 | Sheets et al. | 417/356 X |
| 3,608,088 | 9/1971 | Dorman et al. | |
| 3,938,913 | 2/1976 | Isenberg et al. | 417/356 |
| 3,970,408 | 7/1976 | Rafferty et al. | 415/900 X |
| 4,135,253 | 1/1979 | Reich et al. | 415/900 X |
| 4,507,048 | 3/1985 | Belenger et al. | 415/900 X |
| 4,625,712 | 12/1986 | Wampler | 604/151 |
| 4,688,998 | 8/1987 | Olsen et al. | 415/900 X |
| 4,704,121 | 11/1987 | Moise | 623/3 |
| 4,763,032 | 8/1988 | Bramm et al. | 623/3 X |
| 4,779,614 | 10/1988 | Moise | 415/900 X |
| 4,817,586 | 4/1989 | Wampler | |
| 4,846,152 | 7/1989 | Wampler et al. | 600/16 |
| 4,895,557 | 1/1990 | Moise et al. | 600/16 |
| 4,906,229 | 3/1990 | Wampler | 600/16 |
| 4,908,012 | 3/1990 | Moise et al. | 600/16 |
| 4,944,722 | 7/1990 | Carriker et al. | 600/16 |
| 4,957,504 | 9/1990 | Chardack | 623/3 |
| 4,984,972 | 1/1991 | Clausen et al. | 415/900 X |
| 5,049,134 | 9/1991 | Golding et al. | 415/900 X |

Primary Examiner—Leonard E. Smith
Attorney, Agent, or Firm—Wood, Herron & Evans

[57] ABSTRACT

An axial flow blood pump for intracorporeal or extracorporeal use pumps blood axially through a cylindrical conduit disposed in the bloodstream of a patient. The pump further includes a pump stator mounted in the conduit and a motor stator located either externally or internally of the conduit which applies a magnetic flux in the conduit. A rotor located in the conduit carries permanent magnets which interact with the applied magnetic flux to rotate the rotor. The rotor also carries impeller blades which, during rotation, produces an axial flow of blood through the conduit. During rotor rotation, the rotor is radially suspended solely by one or more hydrodynamic bearings formed by blood flowing through the conduit, with the location of at least one hydrodynamic bearing defined by a radial gap between the inside surface of the conduit and the rotor. By radially suspending, or floating, the rotor on blood in the conduit, the size of the pump may be reduced and the need for radial bearings, radial bearing seals and/or a supply of purge fluid is eliminated.

44 Claims, 14 Drawing Sheets

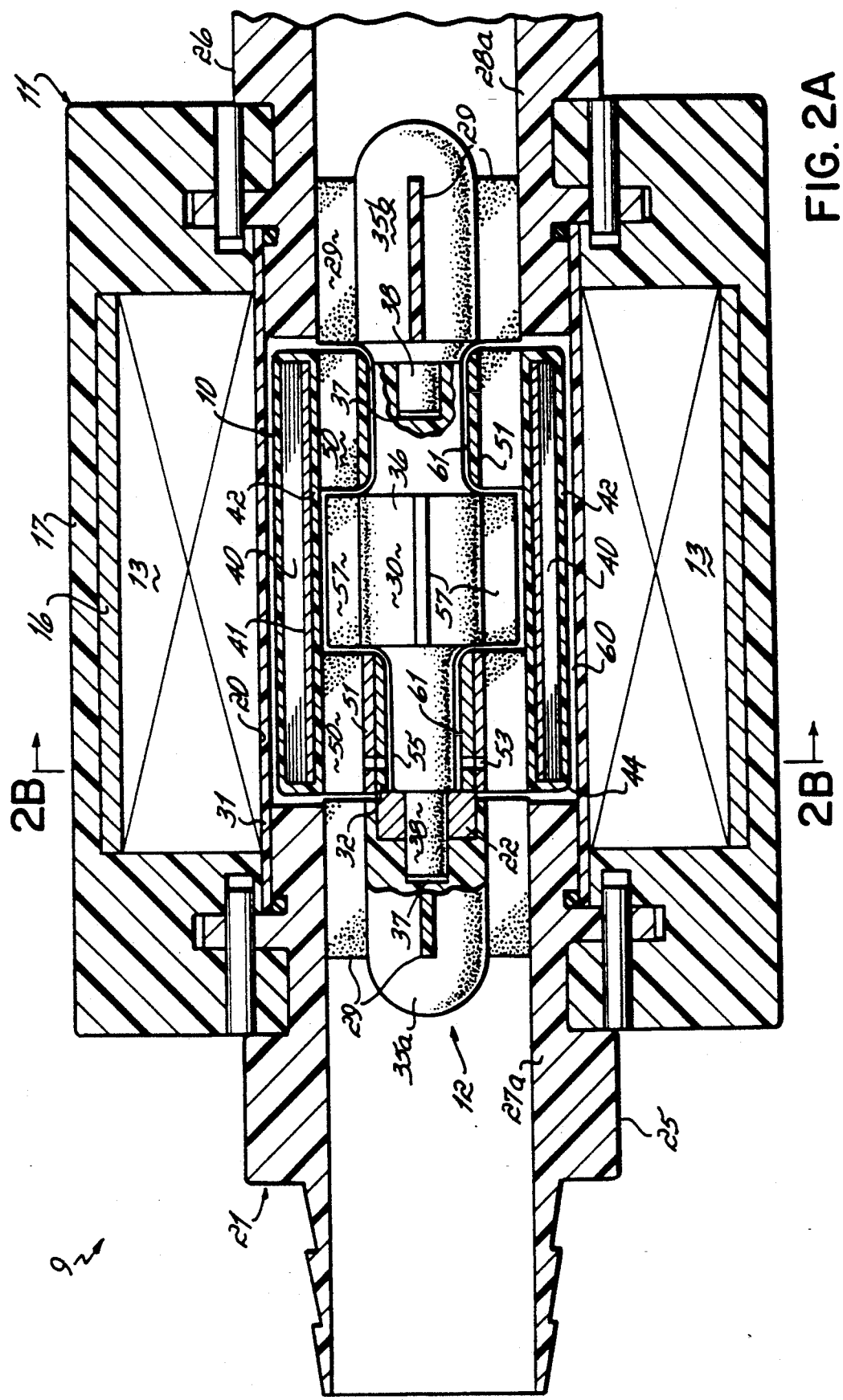

AXIAL FLOW BLOOD PUMP WITH HYDRODYNAMICALLY SUSPENDED ROTOR

This is a continuation-in-part patent application based on applicant's copending U.S. Ser. No. 529,598, filed on May 29, 1990, now U.S. Pat. No. 5,112,200 entitled "Hydrodynamically Suspended Rotor Axial Flow Blood Pump."

BACKGROUND OF THE INVENTION

This invention relates to a blood pump, and more particularly, to a combined axial flow pump and motor that is to be disposed in the bloodstream of a patient to pump or assist in the pumping of blood throughout the patient's circulatory system, either intracorporeally or extracorporeally.

It is desired that a motor/pump of this type have as small a size as possible consistent with the pumping requirements of the device. Suspension of the rotor with respect to the stator is a key to miniaturization. Where it is possible to minimize the structure by which the rotor is suspended with respect to the stator, it becomes possible to minimize the overall diameter of the motor and pump combination.

It is also desired that a motor/pump of this type be constructed which requires neither radial seals that can break down and leak nor radial bearings that require a continuous flow of blood compatible purge fluid. Where it is possible to use a method of suspension of the rotor that operates solely in blood, rotary seals can be avoided and the need to continuously supply purge fluid can be eliminated.

It has been an objective of the present invention to provide an axial flow blood pump with an improved rotor suspension system which minimizes the size of the motor and pump combination, enables the pump to be suspended without radial seals and eliminates the need to continuously supply purge fluid.

This invention contemplates an axial flow blood pump and motor combination which includes a cylindrical housing, or conduit, adapted to be inserted into a patient's bloodstream. The pump and motor combination includes a rotor which, during operation, is radially suspended in the conduit solely by hydrodynamic bearings formed by the pumped blood flowing through the conduit. In effect, the blood "floats" the rotor within the conduit.

In accordance with the present invention, an axial flow blood pump includes a cylindrical conduit to be disposed in the bloodstream of a patient. A pump stator is fixedly mounted coaxially within the conduit and includes inlet and outlet sections, each of which has a set of radially directed stator vanes. A pump/motor rotor resides within the conduit between the inlet and outlet stator sections of the pump stator. A motor stator, located either externally or internally of the conduit, is adapted to create a magnetic flux within the conduit. The rotor carries permanent magnets which interact with the applied flux to rotate the rotor. The rotor also carries impeller blades which, upon rotation of the rotor in the conduit, drive blood from the inlet, through the conduit, and past the outlet. During operation, the rotor is suspended by a hydrodynamic bearing formed by the pumped blood flowing through a radial gap between the inside surface of the conduit and the rotor.

During rotor rotation, the external surfaces, and for some embodiments also the internal surfaces, of the rotor are oriented so that their motion with respect to the conduit and the pump stator fixed therein produce a pressure distribution on the rotor that supports the rotor radially. The pressure distribution also creates a pumping action causing blood to flow through a gap between the rotor and the inside surface of the conduit. Blood flow through this gap is further enhanced by the pressure generated axially across the rotor through the action of the impellers. The axial blood flow past the rotor which is caused by the combined pumping action of the hydrodynamic bearing and the pressure generated by the impellers is hereinafter referred to as leakage flow. The radial gap between the rotor and conduit may be in the range of about 0.001" to about 0.010", and preferably is about 0.003". Since it is this radial gap with the blood flowing through that provides the suspension for the rotor, the radial clearance of the rotor is extremely small. Furthermore, because blood flows directly through the gap which forms this hydrodynamic bearing, neither radial bearings nor radial bearing seals need to be included, nor is purge fluid required for bearing lubrication.

This invention contemplates a number of various structural configurations for radially suspending a rotor within a cylindrical pump housing solely by one or more hydrodynamic bearings. Of these different configurations, several are more suitable for extracorporeal use, while some of the others are more suitable for long term intracorporeal use. Still others may be used advantageously in either mode of operation.

In a first embodiment of the invention, the rotor is cylindrical. Each of the inlet and outlet sections of the pump stator has a plurality of axially-extending vanes with radial inner edges pressed into the external surface of an elongated stator hub which passes through the center of the cylindrical rotor. Located axially between the inlet and outlet stator sections, the cylindrical rotor has an outer surface which cooperates with the conduit inside cylindrical surface. The rotor outer surface and the conduit inner surface create one location wherein the relative radial motion therebetween creates an outer, annular blood flow gap which serves as a hydrodynamic bearing for the rotor. The permanent magnets carried by the rotor are located radially inside of this external blood flow gap.

Intermediate stator vanes, axially spaced from both the inlet and outlet stator vanes, project radially outwardly from the stator hub. On the inlet and outlet sides of the intermediate stator vanes, the stator hub includes two axially spaced reduced diameter portions with annular grooved surfaces. The rotor has two corresponding axially spaced sets of impeller blades. The blades of each set extend radially inwardly from the inside surface of the rotor cylinder, and their radially internal ends terminate in an impeller support ring. The two axially spaced impeller support rings of the impeller blades cooperate with the corresponding axially spaced grooved surfaces of the stator hub to create two axially aligned portions of an internal blood flow gap between the rotor and the stator hub. Thus, with this construction, there is an annular blood flow gap between the rotor outer surface and the conduit inner surface which serves as an outer hydrodynamic bearing, and there are two axially spaced portions of another annular blood flow gap between the two impeller support rings and the stator hub. These portions of this latter gap also serve as additional, inner hydrodynamic bearings for supporting the rotor during rotation.

Each of the axially spaced cylindrical surfaces on the stator hub is in the form of an annular groove that is a shallow U-shape in longitudinal section. Similarly, at the conduit inner surface, the stator inlet and outlet sections cooperate to form a shallow U-shaped annular groove in longitudinal section. These shallow U-shaped grooves axially capture the rotor and maintain it centered radially within the conduit. The force of the impeller tends to drive the rotor axially towards the inlet as it rotates during its blood pumping function. The rearward axial force is frictionally resisted by the engagement of radial surfaces between the rotor and the shallow grooves on the stator hubs and on the stator inlet section. Alternatively, thrust-resisting magnets may be mounted in the stator inlet section to form a thrust-resisting system.

In this first embodiment, and also in a second embodiment, to be described later, a cylindrical rotor is utilized and the impeller blades extend radially inwardly from the pole pieces. This places the pole pieces relatively close to the motor stator, thereby minimizing the magnetic air gap therebetween. The dimension of the magnetic air gap affects the power output of the motor. With all other factors equal, as the magnetic air gap of a motor increases, the power of the motor decreases. Thus, in general, the output of a pump driven by the motor will also decrease.

As explained in the parent application, an axial flow blood pump used as an extracorporeal device requires about 6.0 liters per minute of blood flow at about 300 mg Hg. To some degree, these flow output requirements dictate the structural configuration of the rotor. More particularly, when used extracorporeally, it is best to optimize the power output of the pump by designing a motor and stator configuration which has a minimum magnetic air gap. For this reason, the impeller blades extend radially inwardly from a cylindrical magnet housing.

On the other hand, when used intracorporeally, the motor power output requirement for the pump is significantly lower. While the required blood flow rate remains at about 6.0 liters per minute, the required pressure is lower by about a third, at a value of about 100 mg Hg. With the lower power output required for intracorporeal use, design considerations such as uninterrupted long term use and potential thrombus formation take precedence over the prior, primary consideration of minimizing magnetic air gap.

More specifically, by increasing the magnetic air gap above the dimension utilized in the first two embodiments, the rotor may be made rod-shaped rather than cylindrical and located on a central axis through the pump housing. This shape enables the impeller blades to be located radially outside of the rotor permanent magnets. Compared to the first two embodiments in which blood flows in two widely separated annular paths, both outside and inside a cylindrical rotor, this configuration results in a blood flow path which is entirely outside the radial exterior of the rotor. The third, fourth, fifth, sixth and seventh embodiments utilize a rod-shaped, radially centered rotor to provide an entirely external blood flow path.

Generally, by utilizing a blood flow path around the outside of the rotor, the blood flows in more of a direct line from the inlet to the outlet. Proportionately, radially directed blood flow is reduced, and axially directed blood flow is increased. As a result, the blood flow path is generally straighter, with a reduced possibility that thrombus, or blood clotting, will occur within narrow passages or sharp turns within the structural components of the pump. Generally, such narrow passages pose the greatest threat of blood cell aggregation.

As seen by variations among the third, fourth, fifth, sixth and seventh embodiments, a number of structural modifications of the rotor, the stator and the conduit are possible. The structural differences among these particular embodiments address different concerns related to long term intracorporeal use. However, the most notable of these concerns is that of maximizing the proportion of axially directed blood flow with respect to radially directed blood flow. This enhances the continuous washing of blood contacting surfaces and minimizes stagnation of the blood, thereby reducing the possibility of thrombus.

Additional modifications described in the eighth and ninth embodiments involve the use of a cylindrical rotor, but with the motor stator located inside the conduit and integral with the pump stator, rather than external to the conduit and removed from the pump stator.

For both cylindrical and the rod-shaped rotor embodiments, the invention contemplates the use of a single stage of impeller blades, as opposed to two or even three sets of axially displaced impeller blades. Embodiments ten and eleven relate to an axial flow blood pump with a single stage of impeller blades.

For all embodiments of the axial flow blood pump of this invention, the rotor is radially supported hydrodynamically, solely by the pumped blood. In effect, the blood floats the rotor. In operation, the shear stress and washing action should be high enough to provide sufficient force to prohibit blood cells from aggregating and thereby causing thrombus. However, it is critically important to assure that shear stress is not so high as to cause blood cell destruction.

Furthermore, cell destruction is due not only to shear stress, but also to exposure time of the cells to shear stress. Thus, it is important to provide a rate of leakage flow through the pump which is high enough to minimize residence time of the blood cells in the various gaps. A level of shear stress and exposure time at approximately the threshold level for cell destruction will satisfy both requirements of minimizing thrombus formation and minimizing blood cell destruction. The parameters that contribute to shear stress are the sizes of the gaps which form the flow path, and the velocity of the blood cells through these gaps. Residence time in the gap flow path is dependent upon the overall rate of leakage flow, which in turn is dependent upon the size of each of the gaps. The larger the gap size, the lower is the shear stress and the higher is the rate of leakage flow. Additionally, the greater the proportion of axially directed blood flow with respect to radially directed blood flow, the lesser will be the residence time of the blood cells in the gap. However, if the gaps are too large, the rotor will wobble during rotation. If the gaps are too small, the dwell time will be excessive, and too much viscous friction of the blood cells will be created.

With respect to the first embodiment, in order to minimize cell damage in the gaps, shear stress should be maintained below 2500 dynes per square centimeter and the residence time of blood cells in the outer gap should be below 0.1 second. However, the outer annular gap size must be kept low to minimize violent eccentric motion of the rotor with respect to the stator.

Again, with respect to the first two embodiments, blood cell destruction within the main flow path of the pump, i.e., inside the cylindrical rotor and through the impeller and stator vanes, is also dependent upon shear stress. Since the velocity of a blood cell with respect to the pump stator surfaces affects shear stress, it is sufficient to minimize velocity through the main flow path as a means of minimizing cell destruction. The velocity of blood pumped through the conduit should be below 1000 centimeters per second and preferably below 500 centimeters per second.

It is believed that these velocity parameters may also be applied to the other embodiments of the invention to achieve preferable velocity of blood flow. For each embodiment, the rotational speed of the rotor may be controlled so as to provide the desired velocity of blood flow. For embodiments one, two and ten, to minimize the chance of hemolysis to the blood, it is believed that rotor speed should be in the range of 10,000 to about 13,000 rpm, and preferably as close to about 10,000 rpm as possible. For the third, fourth, fifth, sixth and seventh embodiments, rotor speed should preferably be about 8000 rpm. For the eighth and ninth embodiments, rotor speed should be about 6,000 rpm.

If desired, the rotor may be rotatably driven so as to produce either continuous flow of blood or pulsatile flow of blood. Pulsatile flow may be achieved by cycling the rotational speed of the rotor between a fast and a slow speed at a frequency that corresponds to a human pulse rate.

The features and objectives of the invention will become more readily apparent from the following detailed description and the accompanying drawings.

BRIEF DESCRIPTION OF THE DRAWINGS

FIG. 2A is a diagrammatic longitudinal cross-sectional view through the center of an axial flow blood pump according to a second embodiment of the invention.

DETAILED DESCRIPTION OF THE INVENTION

FIGS. 1A and 1B and FIGS. 2A and 2B depict an axial flow blood pump, according to first and second embodiments, respectively, of the invention. The pump of the first two embodiments is particularly suitable for extracorporeal use, as for instance, in conjunction with a heart/lung machine for open heart surgery, or temporary support following surgery, due to a relatively low magnetic air gap of the motor and the relatively high power output of the pump.

FIGS. 3A and 3B, 4A and 4B, 5A and 5B, 6A and 6B, and 7A and 7B depict third, fourth, fifth, sixth and seventh embodiments of the invention, respectively. In these embodiments, the axial flow blood pump of the invention is generally more suitable for use intracorporeally, either as a left ventricular assist device (LVAD), a biventricular assist device (BVAD), or a total artificial heart replacement.

FIGS. 8A and 8B and FIGS. 9A and 9B depict the eighth and ninth embodiments of the invention, respectively. It is believed that these embodiments would be equally suitable for intracorporeal or extracorporeal use. Due to the capability for miniaturization in size with these two embodiments, it would be possible to introduce the pump into the patient's body intravascularly, through the femoral artery.

Figure 10A:
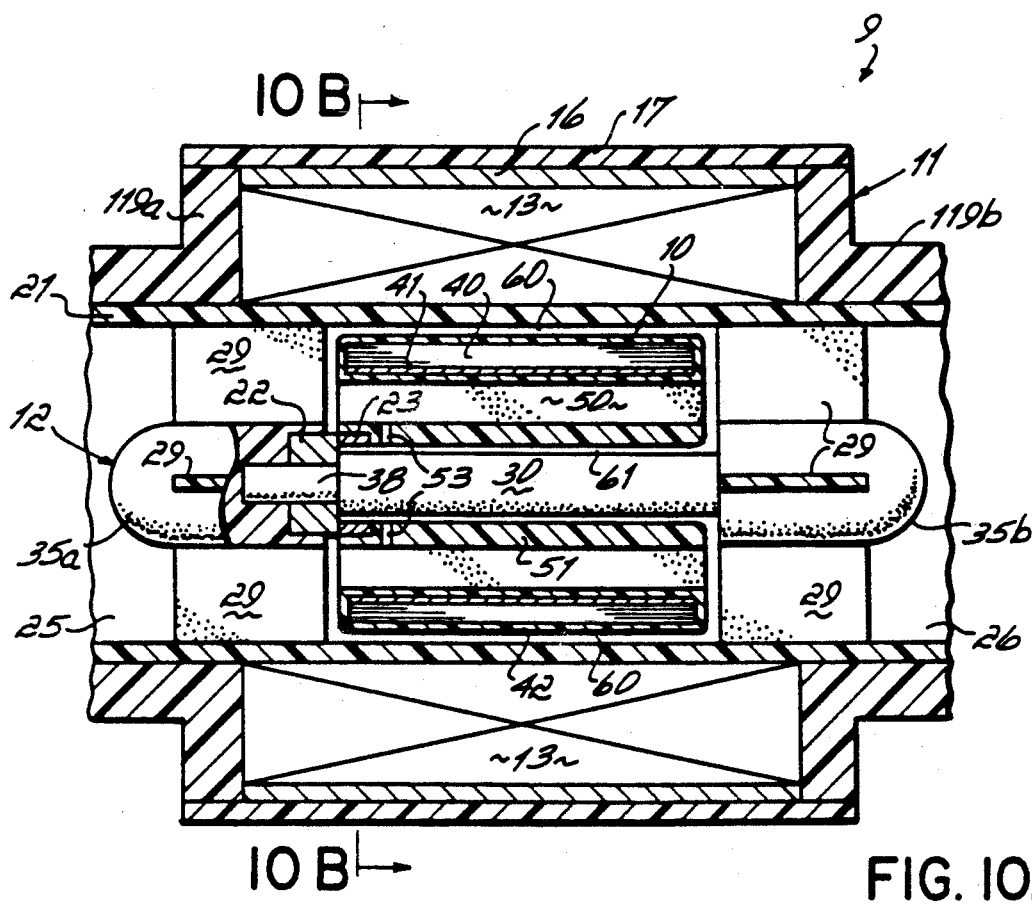
FIG. 10A is a diagrammatic longitudinal cross-sectional view through the center of an axial flow blood pump according to a tenth embodiment of the invention.
Figure 10B:
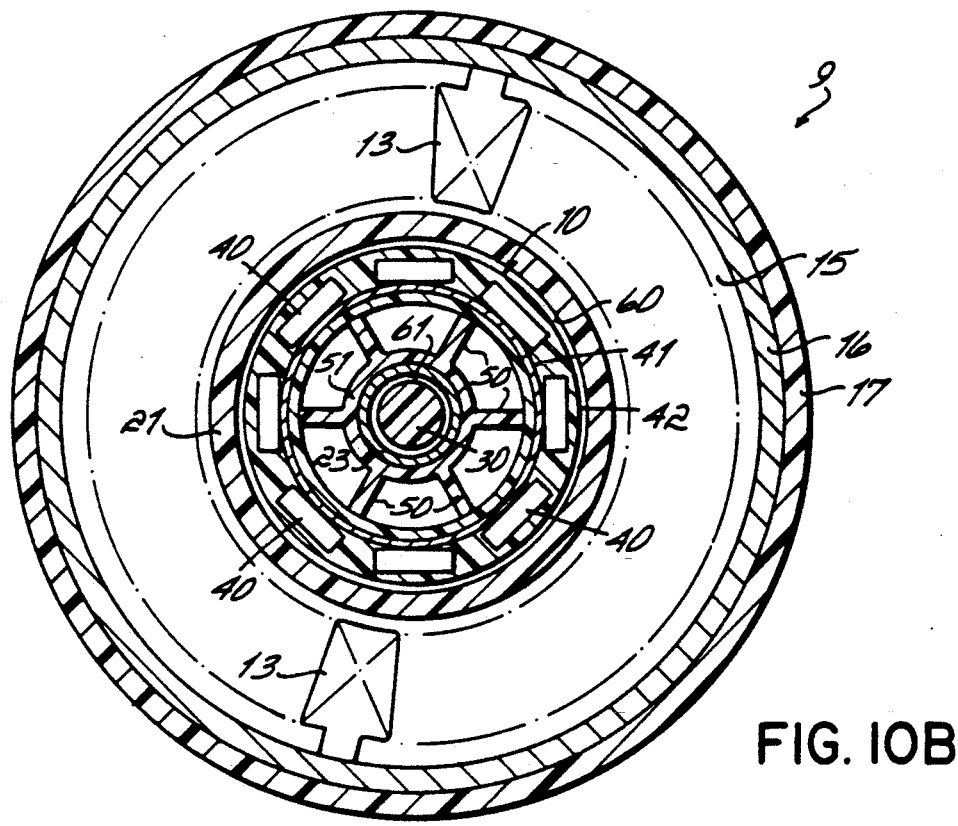
FIG. 10B is a cross-sectional view taken along lines 10B—10B of FIG. 10A.

FIGS. 10A and 10B depict the tenth embodiment of the invention, respectively. This embodiment is a variation of the second embodiment.

I. The First Embodiment

Figure 1A:
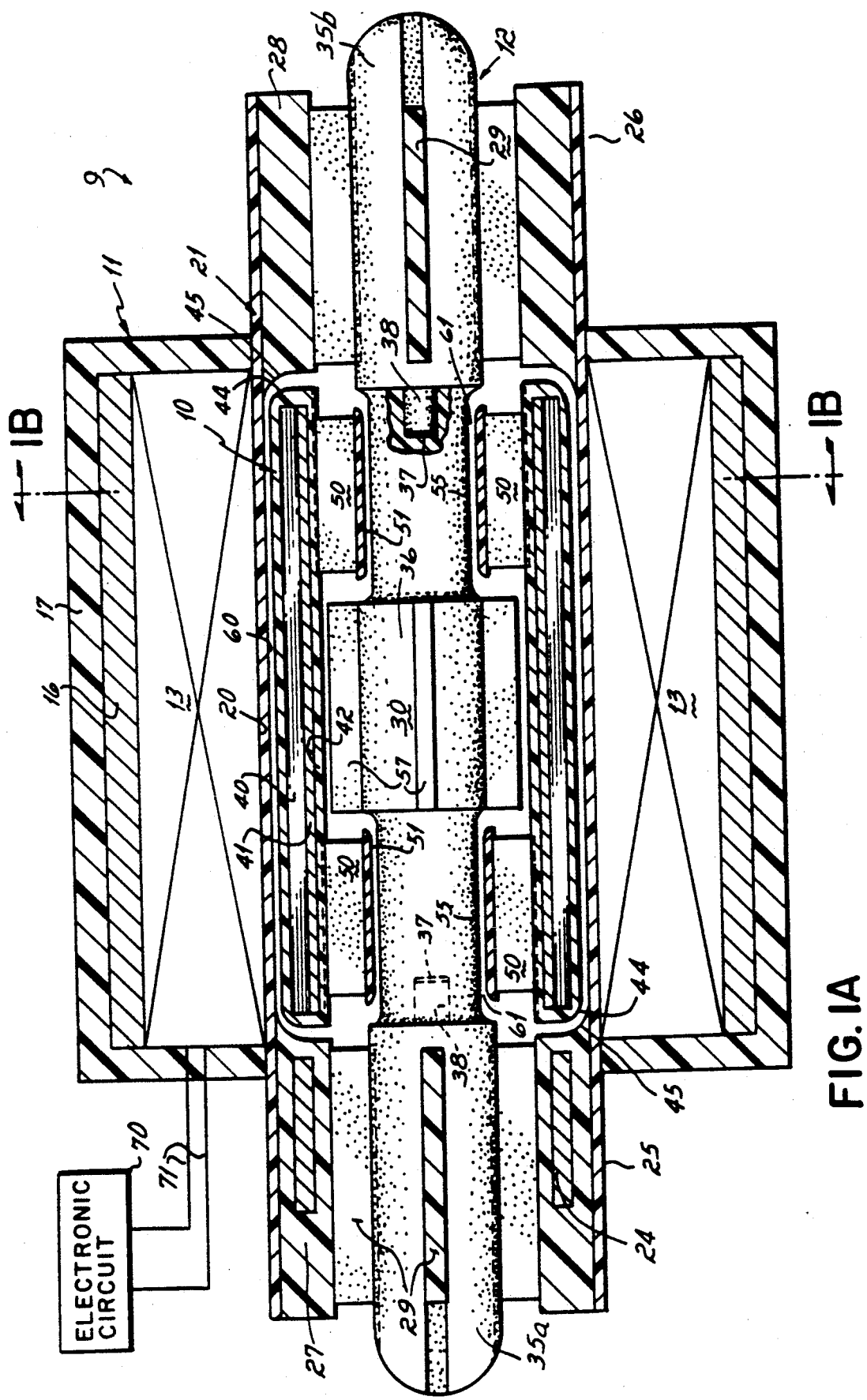
FIG. 1A is a diagrammatic longitudinal cross-sectional view through the center of an axial flow blood pump according to a first embodiment of the invention.
Figure 1B:
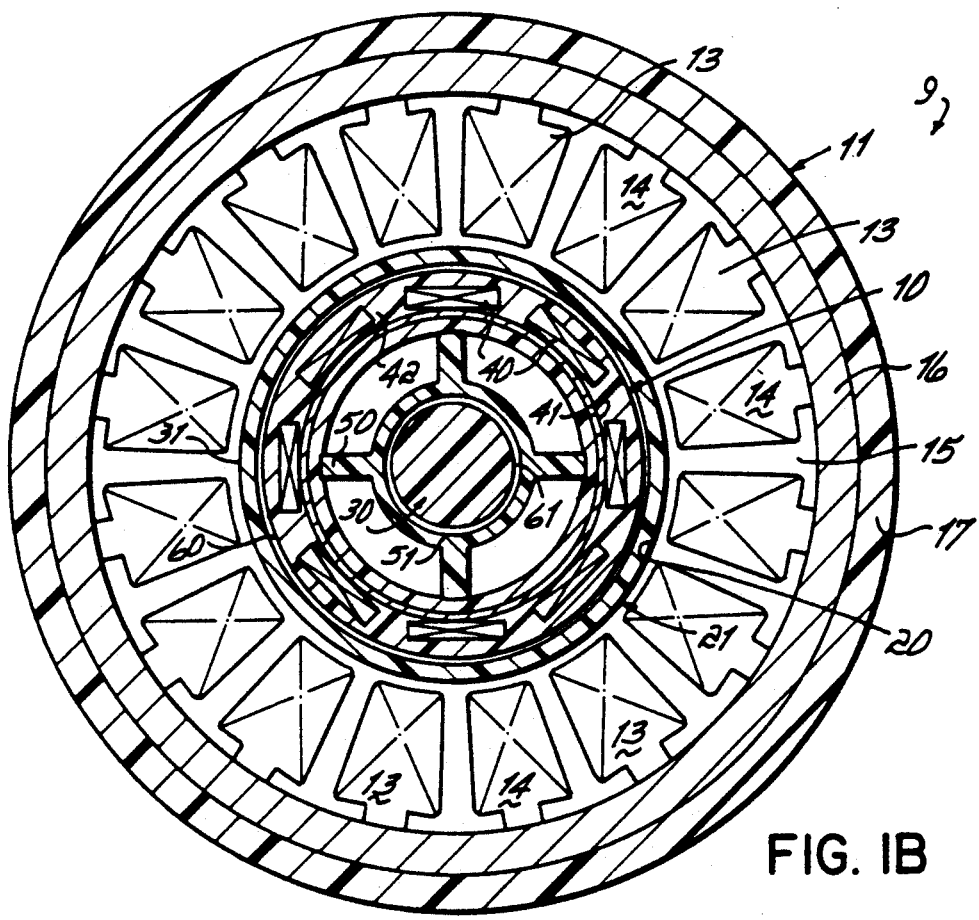
FIG. 1B is a cross-sectional view taken along lines 1B—1B of FIG. 1.

Referring to FIGS. 1A and 1B, an axial flow blood pump is designated generally by reference numeral 9. The pump 9 is identical to the axial flow blood pump described in the parent application. The pump 9 includes a rotor 10 supported within a motor stator 11. The motor stator 11 has phase windings 13 and 14 wound on a stator core 15, as shown in FIG. 1B. A metal yoke 16 surrounds the core 15, and an epoxy encapsulation 17 surrounds the metal yoke 16.

The motor stator 11 has an internal cylindrical surface 20. A plastic housing or conduit 21 is press-fitted into the motor stator 11. The pump stator, designated generally by reference numberal 12, is located in conduit 21. Preferably, the plastic is a thermoplastic polyurethane (ISOPLAST 301 by Dow Chemical), although any one of a number of other blood compatible, non-reactive polymers would also work, such as acrylic or polycarbonate. The conduit 21 has an inlet 25 and an outlet 26. An inlet stator support ring 27 is fixed in the inlet 25, and an outlet pump stator support ring 28 is fixed in the outlet 26. The inlet stator support ring 27 may include a thrust bearing magnet 24 which would oppose a magnet (not shown) mounted in the rotor 10. Each pump stator support ring has six radial vanes 29. The inner ends of the vanes 29 are embedded in the surface of an axially elongated stator hub 30, which is preferably made of plastic.

The stator hub 30 actually has three sections. Inlet and outlet hub sections 35a and 35b, respectively, are connected to a center hub section 36. The center section 36 has axial recesses 37 at each end. The recesses receive studs 38 integral with the inlet and outlet sections 35a and 35b, respectively.

The rotor 10 has eight axially-extending permanent magnets 40 and a back iron ring 41, all of which are embedded in a cylinder of polyurethane plastic resin 42. In this application, all ten embodiments, the rotor 10 carries permanent magnets, though permanent magnets could be used in combination with magnetic soft iron pole pieces. The cylinder 42 is radiused at its ends as at 44. Similarly, the pump stator support rings 27 and 28 are radiused as at 45 to match the ends of the rotor plastic cylinder 42, thereby centering the rotor 10 axially within the conduit 21. The inner diameter of ring 27 and ring 28 is preferably the same as the inner diameter of cylinder 42. The rotor 10 has two sets of impeller blades 50 that are axially spaced from each other. The impeller blades 50 have their inner ends mounted on an inner, impeller support ring 51. The impeller blades 50 have outer ends embedded in the plastic cylinder 42. The hub 30 has a pair of axially spaced, annular grooves 55 into which the impeller support rings 51 fit. Intermediate pump stator vanes 57 are mounted on the hub 30 at the center section 36 and project into the space located axially between the two sets of impeller blades 50.

An outer annular gap 60 is created between the internal surface of the conduit 21 and the plastic cylinder 42 of the rotor 10. This outer gap 60 may range from about 0.001" to about 0.010", though it is presently believed that about 0.003" is the preferable radial dimension. An inner annular gap 61 is formed between each impeller support ring 51 and a corresponding annular groove 55. This inner gap 61 is preferably about 0.010" in radial dimension, though it could also be as low as 0.003". The motion of the rotor 10 within these gaps 60 and 61 provides a pressure distribution on the rotor 10, thereby creating hydrodynamic bearings that maintain the rotor 10 substantially centered radially in the conduit 21 and the motor stator 11. The length of gap 60 is preferably about 1". The length of each gap 61 is preferably about 0.3". It is now believed that the preferable inside diameter of the conduit 21 should be 0.585". The preferable diameter of the annular grooves 55 is about 0.230".

To assemble the axial flow blood pump 9, the impeller blades 50 are pressed axially into the internal surface of the plastic cylinder 42 with the center hub section 36 carried between the impeller blades 50. The pump stator vanes 29 are then axially-pressed into the stator support rings 27 and 28. With the rotor 10 centered in the conduit 21 and carrying hub center section 36, the two opposite sides which form the rest of the pump stator assembly 12, i.e., pump stator support rings 27 and 28, vanes 29 and hub ends 35a and 35b, are pressed into opposite sides of the conduit 21 until the studs 38 of hub sections 35a and 35b seat in the two recesses 37 of the hub center section 36.

In FIGS. 1A and 1B, the intermediate pump stator vanes 57 have free edges. The radial clearance between the free edges of the stator vanes 57 and the rotor 10 inside surface is preferably about 0.0045", but could possibly be as great as 0.010". The gap at the edge of the vanes 57 also serves as another intermediate hydrodynamic bearing. It is also contemplated that the pump stator vanes 57 could be encased in a plastic ring. This would close off, or further define, this gap between the center stator section 36 and the plastic cylinder 42, so that it would serve as an enhanced, intermediate hydrodynamic bearing. For this variation, the radial dimension of the vanes 57 would have to be reduced to accommodate the ring and still provide the same radial clearance.

It should be understood that the impeller blades 50 and stator vanes 57 are preferably axially angulated, or spiraled, so as to gently thrust fluid from the inlet 25 to the outlet 26.

The motor stator 11 is connected to an electronic circuit 70 by leads 71 and the brushless DC motor formed by motor stator 11 and rotor 10 is operated generally in accordance with the principles of U.S. Pat. Nos. 4,027,215, 4,238,717, 4,492,903 and 5,099,182 which are incorporated herein by reference.

In the operation of the first embodiment of the invention, the axial flow blood pump 9 is connected to a patient's circulatory system, preferably externally. A power supply and electronic circuit 70 connected to the motor stator 11 generate a magnetic flux within the conduit 21 which interacts with the magnets 40 to rotatably drive the rotor 10.

The impeller blades 50 on the rotor 10 drive blood axially through the center of the conduit 21, thereby substituting for or assisting the heart and maintaining the patient's needed circulation. The action of the impeller blades 50 creates a high pressure at the outlet 26 of the conduit 21 and a low pressure at the inlet 25 of the conduit 21. The high pressure differential causes leakage flow of blood through the gaps 60 and 61. It is calculated that the residence time of a cell in the gap 60 is about 0.034 seconds, and the residence time of a cell in each gap 61 is about 0.013 seconds. The shear stress in the gap 60 is about 1900 dynes per square centimeter, and the shear stress in the gap 61 is about 2200 dynes per square centimeter.

II. The Second Embodiment

Figure 2B:
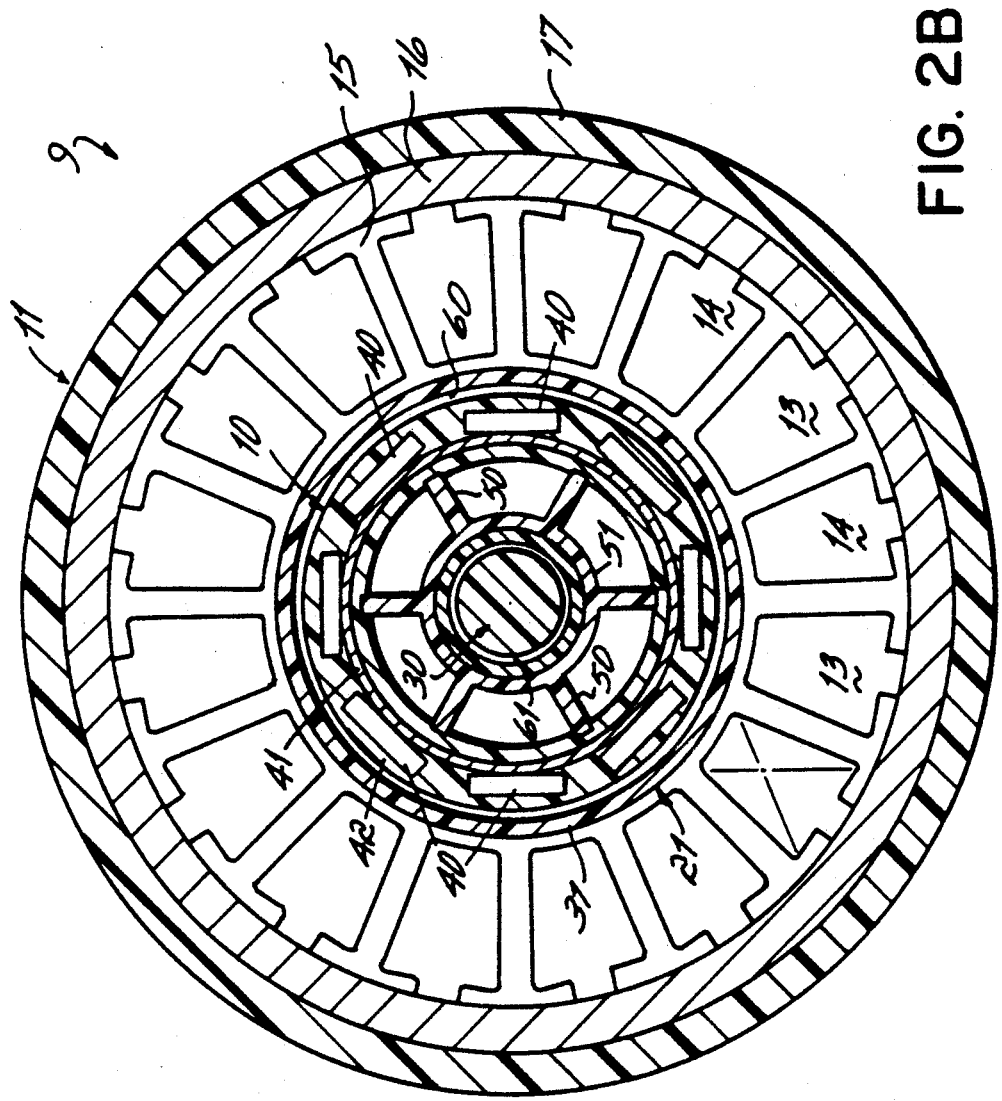
FIG. 2B is a cross-sectional view taken along lines 2B—2B of FIG. 2A.

The second embodiment is shown in FIGS. 2A and 2B. The reference numerals used in FIGS. 2A and 2B and in FIGS. 1A and 1B correspond to similar structural components. Some additional reference numerals used in FIGS. 2A and 2B, but not in FIGS. 1A and 1B, reflect structural components included in the second embodiment, but not in the first.

The second embodiment differs from the first embodiment in a number of respects. First, hub 30 has a reduced diameter adjacent inlet 25, compared to the diameter adjacent outlet 26. This enables an impeller thrust bearing support ring 32 to be mounted radially inside of the ring 51 located adjacent the inlet 25. An inlet directed annular surface of the ring 32 coacts with an outlet directed annular surface of thrust bearing element 22 mounted within hub inlet section 35a, thereby to form an annular thrust bearing during blood pumping. The axial clearance between the impeller blades 50 and radial vanes 29, and between impeller blades 50 and the other components of inlet section 35a is preferably about 0.003", but there is zero clearance between the ring 32 and the thrust bearing element 22 of hub inlet section 35a. In one approach, the coacting surfaces of the thrust bearing may be of dissimilar materials, such as ceramic and 17-4 PH hardened stainless steel, thereby to promote smooth rotational movement. In another approach, the surfaces are of an identical, but very hard, material such as diamond or jeweled bearings.

Because there is zero clearance at the location of the coacting thrust bearing surfaces, a plurality of radially directed throughholes 53 must be formed in ring 51 and ring 32 to permit blood flow into gap 61. The number of holes 53 equals the number of impeller blades 50 which is preferably four. Each hole 53 is located halfway between every two impeller blades 50. Preferably, these holes 53 have a diameter of about 0.052" and are located about 0.046" from the inlet ends of the impeller support ring 51 and ring 32.

Adjacent the outlet, hub 30 has a larger diameter so that annular gap 61 preferably has a dimension of about 0.010" at both the inlet 25 and the outlet 26.

With the second embodiment, the conduit 21 is formed by a plurality of axially aligned components, rather than one cylindrical piece. More particularly, conduit 21 is formed by a sleeve 31, a stator support section 27a at the inlet 25 and a stator support section 28a at the outlet 26. In the Figures, sleeve 31 is a plastic such as thermoplastic polyurethane (ISOPLAST 301 by Dow Chemical), because it is believed that a hermetically sealed plastic would work better than a blood compatible stainless steel, due to the absence of eddy currents. Alternatively, any other blood compatible non-reactive polymer may also be substituted. Tubing (not shown) in communication with the patient's bloodstream connects to external surfaces of the stator support sections 27a and 28a. Sections 27a and 28a preferably have an inner diameter of about 0.375", which is identical to the inner diameter of the rotor cylinder 42. This inner diameter is also identical to the diameter of sections 27 and 28 of the first embodiment. The rotor 10 resides within the sleeve 31, which has an inner diameter of 0.585". At the inlet and the outlet, the axial clearance between the rotor 10 and the inner ends of sections 27a and 28a, respectively, is preferably about 0.020". The cylinder 42 of the rotor 10 has an outer diameter which is less than that of the sleeve 31. The cylindrical 42 outer diameter is greater than the inner diameter of the section rings 27a and 28a. Preferably, the radial dimension of the annular gap 60 between the rotor 10 and the sleeve 31 is about 0.0035", and the magnetic air gap is about 0.045".

In this embodiment, the radial clearance between the free edges of the intermediate stator vanes 57 and the rotor 10 internal surface is preferably about 0.0045". Consistent with dimensions at the inlet, the axial clearance between the impeller blades 50 and the outlet section 35b is preferably about 0.003". Similarly, the axial clearance between the stator vanes 57 and the impeller blades 50 is preferably about 0.003". It is to be understood that varying one of these gap dimensions would most likely necessitate varying the others.

The pump 9 is assembled in the same manner as described above with respect to the first embodiment. The impeller blades 50 are press fit into cylinder 42, with center portion 36 carried axially therebetween. The rotor 10 is then axially centered within sleeve 31 and the remaining inlet 27a and outlet 28a portions of the pump stator 12 are then connected within the ends of sleeve 31 and into the ends of the hub 30. Though not indicated by reference numerals, FIG. 2B shows additional structural details for connecting a motor 11 which is split into two halves. The details are described in applicant's copending application Ser. No. 654,833, entitled "Split Stator For Motor/Blood Pump," filed on Feb. 13, 1991, which is expressly incorporated herein by reference in its entirety. While this split stator may be used in connection with this invention, it is not a feature of the present invention.

In FIG. 2B, the phase windings 13 and 14, the core or lamination stack 15, the yoke rings 16, the encapsulation 17, and the power supply and circuit 70 and leads 71 (shown in FIG. 1A) of the motor stator 11 are identical to those of the first embodiment. Similarly, the cylinder 42 is resin and encapsulates pole pieces and/or magnets 40 and back iron ring 41, as shown in FIGS. 2A and 2B.

In operation, the axial flow blood pump of the second embodiment works in the same manner as the first.

Thus far, the invention has been described as having a cylindrical rotor 10 located within the motor stator 11 and a pump stator located at inlet and outlet ends of the rotor 10, and extending through the cylindrical rotor 10. However, as explained previously, it should be understood that the principles of the invention are also applicable to a number of other motor/pump combinations which structurally differ from the first and second embodiments, but which still employ an axial flow blood pump/motor with a rotor 10 that is rotatable within a conduit solely on at least one hydrodynamic bearing formed by blood pumped through the conduit 21.

III. The Third Embodiment

Figure 3A:
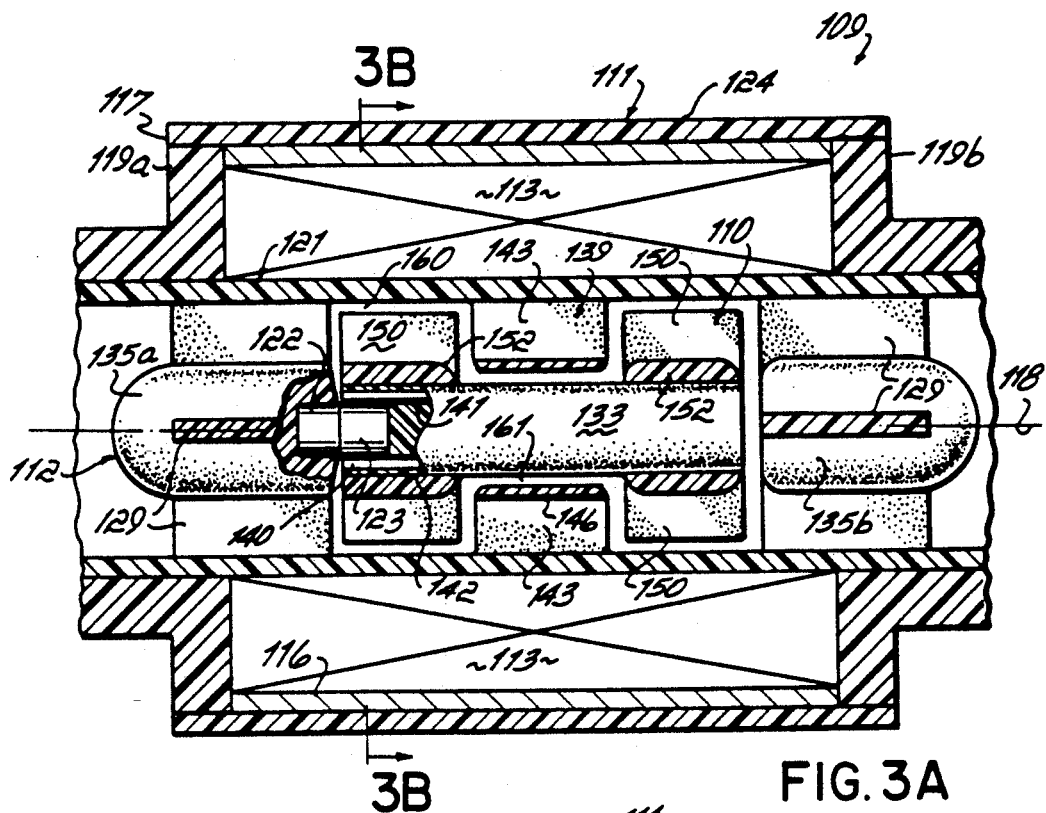
FIG. 3A is a diagrammatic longitudinal cross-sectional view through the center of an axial flow blood pump according to a third embodiment of the invention.
Figure 3B:
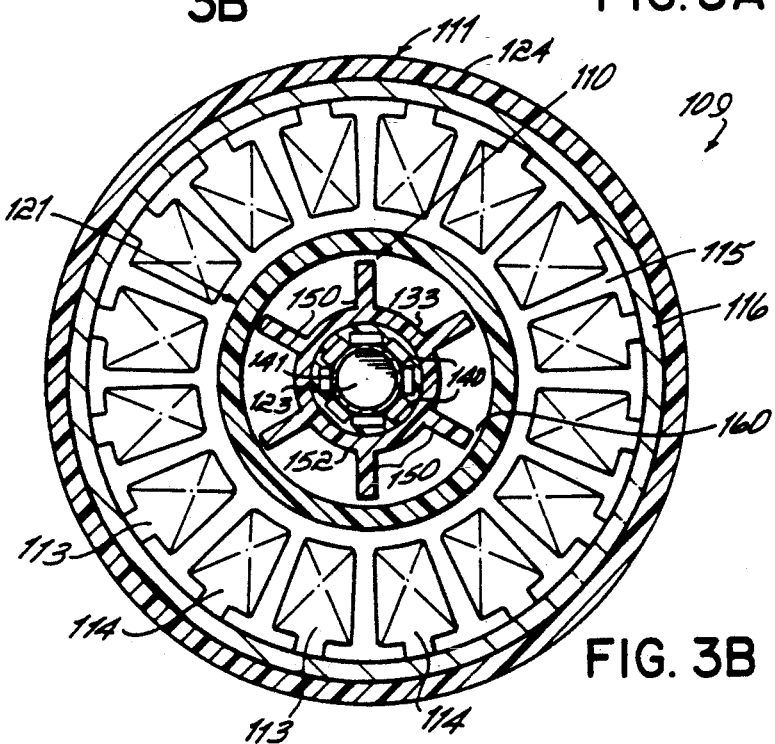
FIG. 3B is a cross-sectional view taken along lines 3B—3B of FIG. 3A.

In the third preferred embodiment, depicted in FIGS. 3A and 3B, the reference numerals have three digits and begin with the numeral "1". These "100" series reference numerals are also used to identify components used in the fourth, fifth, sixth and seventh embodiments, wherein the rotor 10 is not cylindrical and does not circumscribe the pump stator. Rather, in these embodiments, the rotor 10 is solid, rod-shaped and occupies the radial center of the blood passageway. As indicated previously, embodiments three through seven are more suitable for intracorporeal use.

Components common to embodiments one and two (cylindrical rotor) and embodiments three through seven (noncylindrical) can be identified by the last two digits of the respective reference numerals. For example, the motor stator is identified by numeral 11 in FIGS. 1A, 1B, 2A and 2B and by numeral 111 in FIGS. 3A–7B.

FIG. 3A shows an axial flow blood pump 109 in accordance with the third embodiment. A motor stator 111 surrounds a cylindrical conduit or sleeve 121, which serves as the passageway through which blood is pumped. The axial ends of the conduit 121 connect to tubes (not shown) which are in fluid communication with the patient's blood stream. The conduit 121 has an inner diameter of about 0.585", which is identical to the inner diameter of tube conduit 21 and second sleeve 31 of the first two embodiments, respectively. In the third embodiment, as with the other embodiments, blood contacting components are shown as plastic because it is believed that the optimum blood compatible material would be plastic, though other materials would also work.

A rotor 110 is located in the conduit 121 and centered along an axis 118 therethrough. The rotor 110 is located axially between pump stator inlet section 135a and pump stator outlet section 135b. The inlet and outlet stator sections 135a and 135b have radially outwardly extending vanes 129 which are press fit into the inner surface of the conduit 121.

An outlet directed surface of the inlet section 135a coacts with an inlet directed surface of the rotor 110 to form a thrust bearing for axially supporting the rotor 110 during rotation. More specifically, a radially centered thrust bearing element 122 is located within the outlet directed surface of the pump stator inlet section 135a, and a radially centered thrust bearing element 123 is carried by the rotor 110. According to one approach, both of the elements 122 and 123 is pointed and the other is arcuately hollowed to accommodate the point, thereby forming a type of ball-and-socket joint. In another approach, both of the elements 122 and 123 are hard and flat. Preferably, one of the elements 122 and 123 is ceramic while the other is of hardenable, blood compatible stainless steel, thereby to promote low wear and substantially frictionless rotatable movement therebetween. According to another approach, both elements 122 and 123 are of a very hard material, such as diamond, or jewel bearings.

At axis 118, there is no axial clearance between the thrust bearing elements 122 and 123. The axial clearance between the rotor 110 and inlet section 135a increases, either continuously or stepwise, with radial distance away from the axis 118. Preferably, the distance between the inlet stator section 135a and the impeller blades 150 is about 0.003". The clearance between the outlet stator section 135b and an outlet end of the rotor 110 is preferably about 0.003". These axial clearances should be sufficient to provide continuous washing of the surfaces via rotor motion and centrifugal forces, thereby to prevent thrombus formation.

The rotor 110 includes a rod-shaped midportion 133 from which two sets of axially spaced impeller blades 150 extend radially outwardly. For additional stability, each set of impeller blades 150 extends outwardly from a thickened rotor hub portion 152. The outer ends of the impeller blades 150 preferably have a radial clearance of about 0.0035" from the inside surface of conduit 121. This clearance provides an outer annular gap 160 between the impeller blades 150 of the rotor 110 and the conduit 121 which serves as a hydrodynamic bearing during rotor 110 rotation.

An intermediate stator section, designated generally by reference number 139, resides in the conduit 121 and is located axially between the two sets of impeller blades 150, with preferably about 0.003" of axial clearance at both the inlet and outlet directed ends thereof. The intermediate stator section 139 includes radial vanes 143 with outer ends which press fit into the conduit 121 and inner ends which terminate in a support hub 146. The radial clearance between hub 146 and midportion 133 forms an inner annular gap 161 which serves as a hydrodynamic bearing during rotor 110 rotation. Preferably, the inner annular gap 161 has a radial dimension of about 0.010", but could be as low as 0.0045".

Preferably, the upstream and downstream edges of the support hub 146 are radiused, or smoothly contoured. Similarly, impeller hubs 152 are also contoured. These contours promote free, uninterrupted blood flow through conduit 121 during pumping, a feature which is particularly advantageous in minimizing hemolysis when the pump 109 is used for a long term, as is typical for intracorporeal use.

The motor stator 111 is located radially externally of conduit 121 and is further encased axially between inlet and outlet annular flanges 119a and 119b and radially inside of an outer sleeve 124. Like the motor stator 11 of embodiments one and two, which included a yoke 16 surrounded by an encapsulate 17, the motor stator 111 in embodiments 3, 4, 5, 6 and 7 has a yoke 116 surrounded by an encapsulate which is designated generally by reference numeral 117. Encapsulate 117 includes includes outer sleeve 124 and flanges 119a and 119b. Preferably, conduit 121, flanges 119a and 119b and sleeve 124 are of lightweight, hermetically sealed plastic so as to be leak proof for blood compatible intracorporeal use. However, these components may also be of stainless steel, or any other blood compatible material.

Motor stator 111 includes phase windings 113 and 114, a lamination stack or core 115, yoke rings 116, a power supply and circuit and leads (not shown), similar to the stator 11 of the first two embodiments. Though not shown, one of flanges 119a or 119b is machined through to provide access for connecting electrical leads to the windings 113 and 114. It is to be understood that, within midportion 133, the magnets 140 could be sized to occupy the largest possible volume, thereby to generate a magnetic field of maximum strength.

Axially elongated magnets 140 are located within the midportion 133. Preferably, eight permanent magnets 140 extend substantially along the entire axial length of the midportion 133, and a back iron ring 141 is located radially inside the magnets 140. The radial magnetic air gap between the magnets 140 and the motor stator 111 is about 0.060".

Alternatively, the impeller blades 150 could be of soft iron, which is magnetizable, thereby to serve as pole pieces which would extend radially outwardly from midportion 133 and further reduce this air gap.

To assemble the pump 109 of this embodiment, the intermediate stator section 139 is press fit within conduit 121, with the rotor 110 carried thereon. With the rotor 110 axially centered, the remainder of the pump stator 112 components are connected within the inlet and outlet ends of conduit 121.

In operation, as with the first two embodiments, the motor stator 111 is connected to the electronic circuit (not shown) by leads (not shown) through one of the flanges 119a or 119b and the brushless DC motor is operated in accordance with the principles of U.S. Pat. Nos. 4,027,215; 4,238,717 4,492,903 and 5,099,182. As stated previously, to obtain acceptable shear stress and residence time values for minimizing blood cell damage, and in order to produce appropriate flow and pressure, the rotor 110 should preferably be operated to rotate the rotor 110 in the range of about 8,000. This rotational speed is also preferable for the fourth, fifth, sixth and seventh embodiments.

Because of the lower output requirements when used intracorporeally, a greater radial magnetic air gap is acceptable, compared to the first and second embodiments. It is this lower power requirement which enables the magnets 140 to be located within midportion 133 and thus inside of the impeller blades 150.

As a result of this configuration, the blood flow path is entirely outside of the axially centered rotor midportion 133, and it is more direct. The reduction in radially directed blood flow and undesired flow into narrow passages reduces the possibility that thrombus will occur during blood flow through the conduit 121. For these reasons, this embodiment is more suitable for temporary support, or long term use, as a LVAD, a BVAD, or as a total artificial heart replacement.

IV. The Fourth Embodiment

Figure 4A:
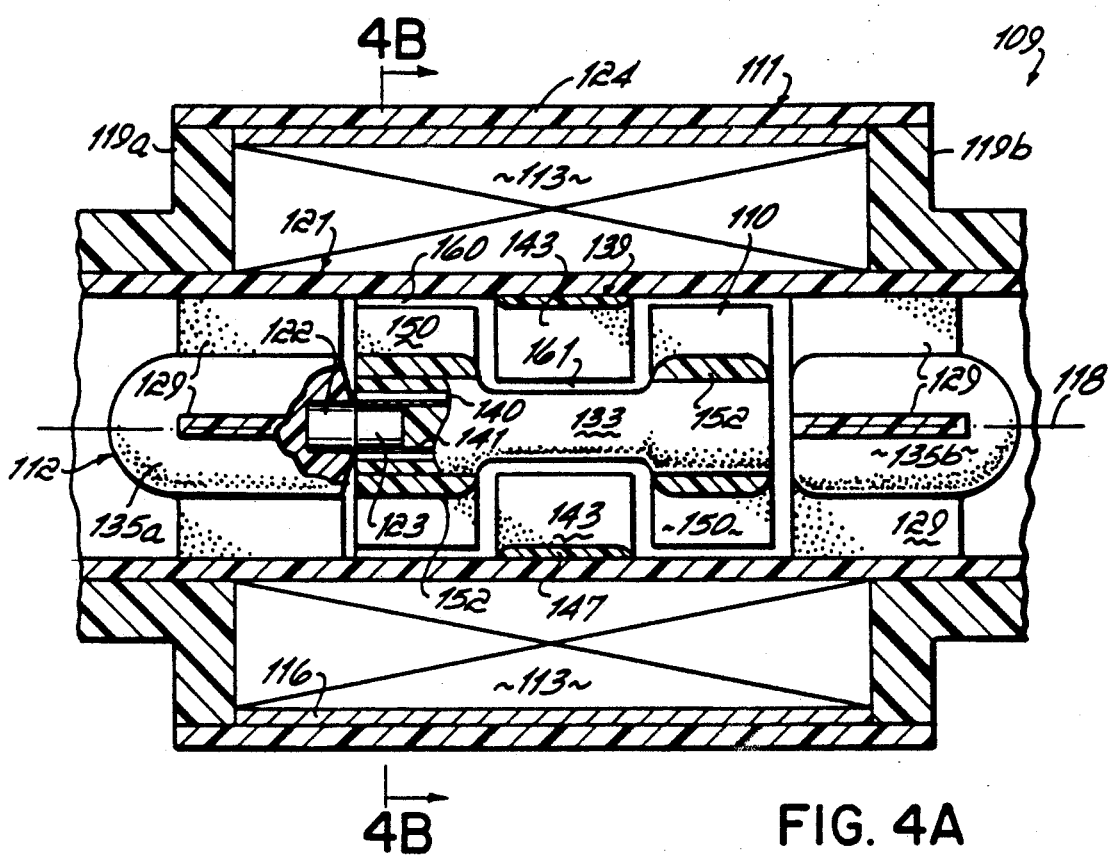
FIG. 4A is a diagrammatic longitudinal cross-sectional view through the center of an axial flow blood pump according to a fourth embodiment of the invention.
Figure 4B:
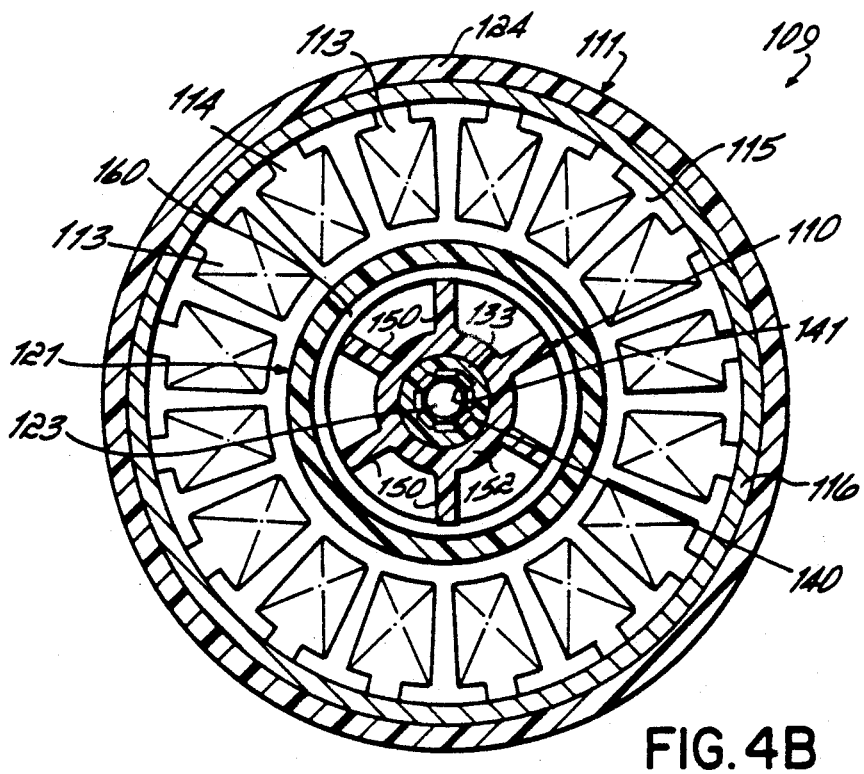
FIG. 4B is a cross-sectional view taken along lines 4B—4B of FIG. 4A.

FIGS. 4A and 4B show a fourth embodiment of the invention. The fourth embodiment is very similar to the third embodiment, except for some variation in the intermediate stator section 139 and additional contouring of the rotor midportion 133. In transverse cross-sectional view, the thrust bearing of the third and fourth embodiments are identical, as shown by FIGS. 3B and 4B.

More specifically, the hub 146 shown in FIG. 3A has been removed, and an external ring 147 has been press fit inside the conduit 121. The outer radial ends of the vanes 143 of the intermediate stator 139 terminate in the ring 147, and the inner radial ends of the vanes 143 are free. Preferably, the inner ends of the vanes 143 have a radial clearance of about 0.0045" from the midportion 133, thereby defining an inner annular gap 161. The radial clearance between the impeller blades 150 and conduit 121 defines an outer annular gap 160, which is preferably about 0.0035". The gap 160, and inner gap 161, may range from 0.001" to 0.010". At its inlet and outlet ends, the axial clearance between the vanes 143 and the impeller blades 150 is preferably about 0.003".

With an external ring 147, rather than an internal hub 146 (as shown in FIGS. 3A and 3B), the blood is not divided into two annular paths by the intermediate stator 139. This singular path structure further reduces hemolysis and the possibility of thrombus formation during blood pumping.

Compared to the third embodiment, the midportion 133 of the fourth embodiment is thinner and more contoured in order to equalize the blood path through the entire length. As a result, the magnets 140 of the rotor 110 must be located slightly further radially inward, resulting in a slightly greater magnetic air gap.

The axial clearance between the outlet end of the rotor 110 and the outlet stator section 135b is preferably about 0.003", while the axial clearance at the inlet end remains the same as described previously with respect to the third embodiment, i.e., preferably about 0.003" and decreasing, either continuously or stepwise, to zero at axis 118. The pump 109 of the fourth embodiment is assembled in the same manner as the third embodiment.

V. The Fifth Embodiment

Figure 5A:
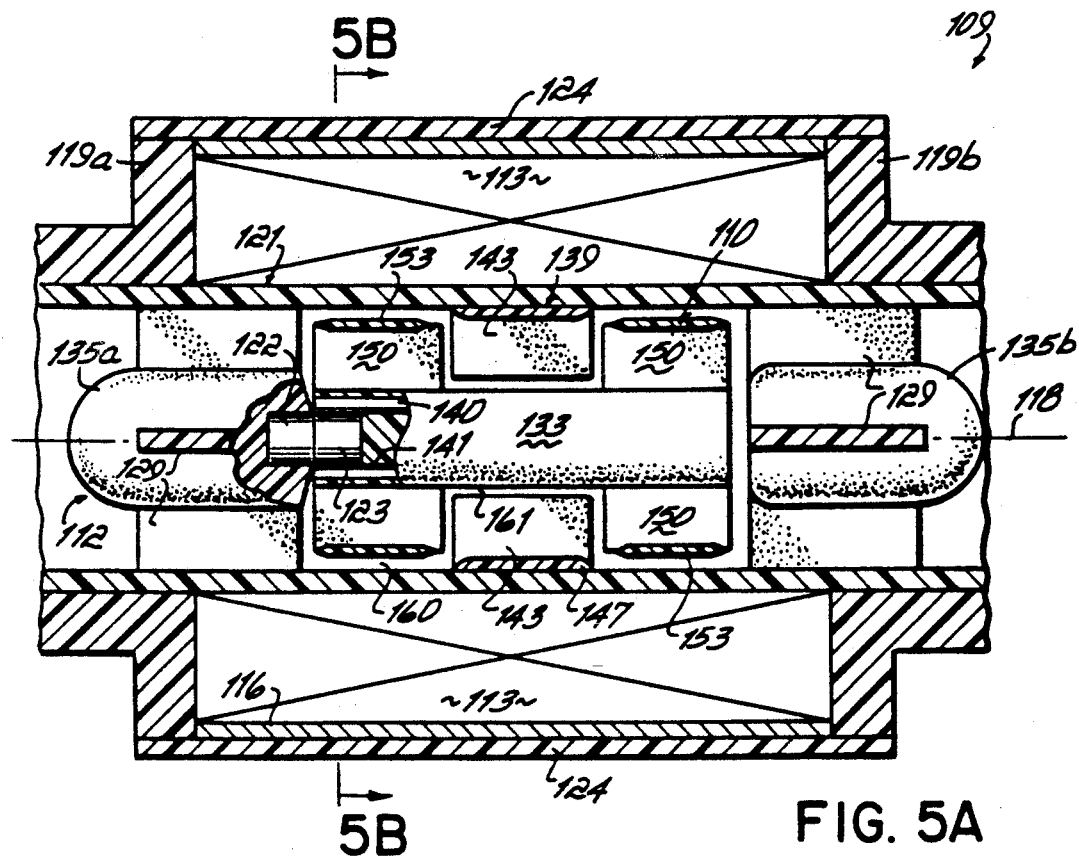
FIG. 5A is a diagrammatic longitudinal cross-sectional view through the center of an axial flow blood pump according to a fifth embodiment of the invention.
Figure 5B:
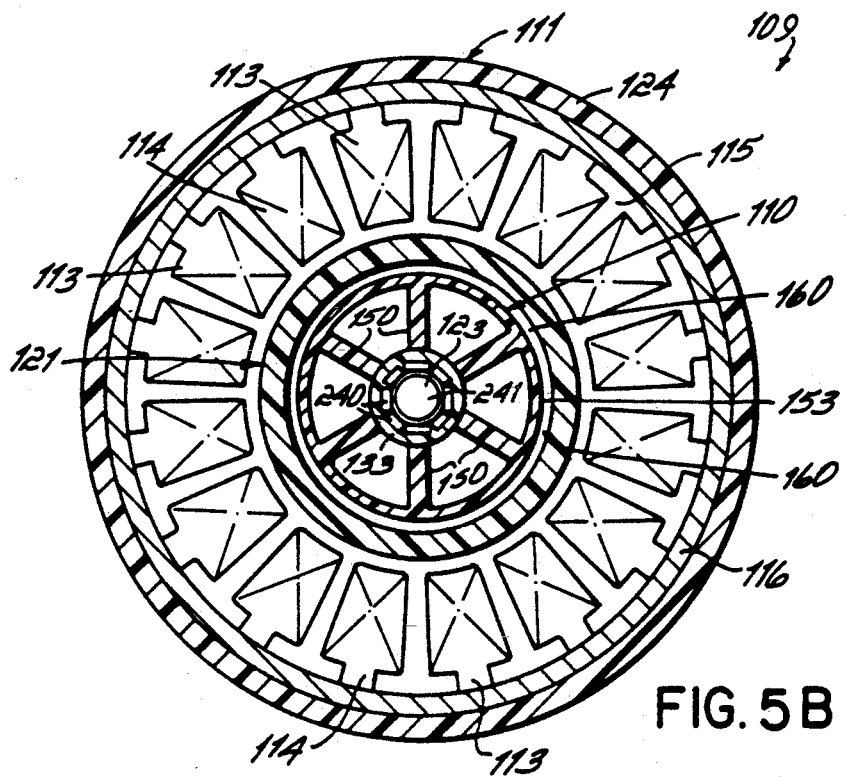
FIG. 5B is a cross-sectional view taken along lines 5B—5B of FIG. 5A.

FIGS. 5A and 5B shows a fifth embodiment of the invention, which is a hybrid between the third and fourth embodiments.

Like the third embodiment, the midportion 133 is uniform in cross-sectional thickness along its length. The axial clearance dimensions of the inlet and outlet ends of the midportion 133 are the same as those of the third embodiment. That is, at the outlet, the axial clearance is preferably about 0.003". At the inlet, the axial clearance is also 0.003", but decreases continuously or step-wise to zero at axis 118.

Like the fourth embodiment, the intermediate stator section 139 has an outer ring 147. However, unlike either the third or fourth embodiments, each set of impeller blades 150 also includes an outer support ring 153. These rings 153 each have a radial clearance of about 0.0035" from the inside surface of the conduit 121 when the rotor 110 is radially centered, thereby defining two axially spaced portions of an outer annular gap 160 between the conduit 121 and the rotor 110 which serves as a hydrodynamic bearing during blood pumping. The rings 153 divide blood flow into separate annular paths. An inner annular path 161 between rotor 133 and vanes 143 has a preferable radial clearance of about 0.0045" when the rotor 110 is centered in sleeve 121.

To minimize the hemolysis effect that two separate paths may have on the blood cells, the inlet and outlet ends of the rings 153 are preferably contoured. If desired, the contouring of rings 153 may extend only partially along the entire axial length of the respective sets of impeller blades 150, as shown in FIG. 5A. In this manner, the axial clearance between the outer ring 147 of intermediate stator 139 and each of the support rings 153 would be about 0.020". At its inlet and outlet ends, the axial clearance between the intermediate stator vanes 143 and each of the sets of impeller blades 150 is preferably about 0.003".

The fifth embodiment is assembled in the same manner as the third and fourth embodiments.

VI. The Sixth and Seventh Embodiments

Figure 7B:
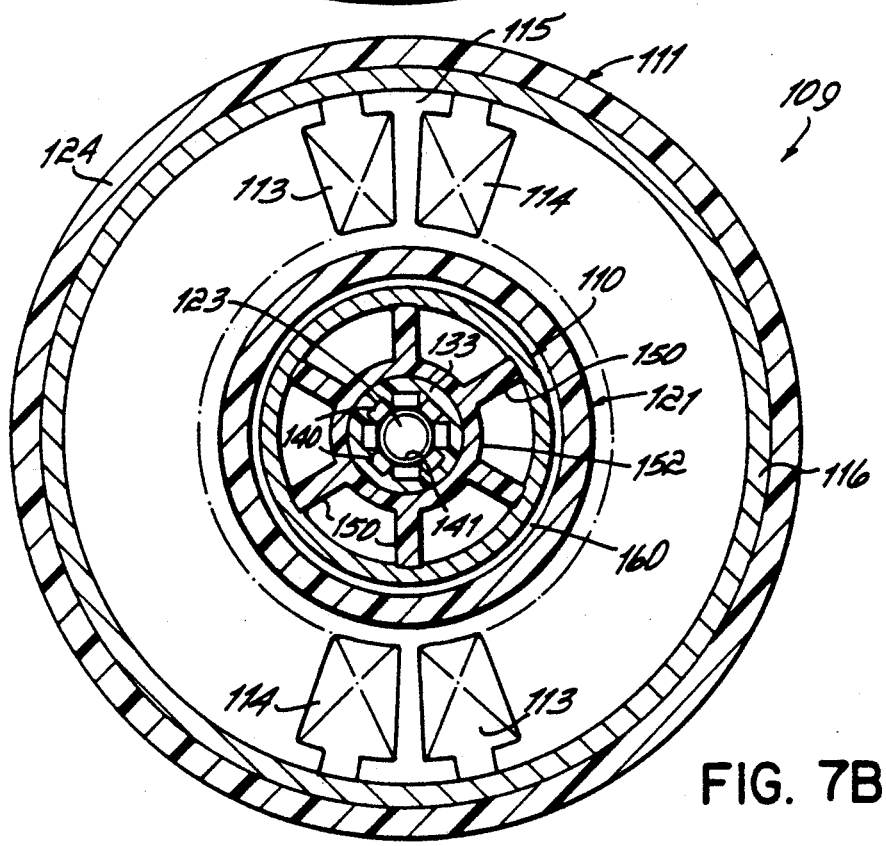
FIG. 7B is a cross-sectional view taken along lines 7B—7B of FIG. 7A.
Figure 6A:
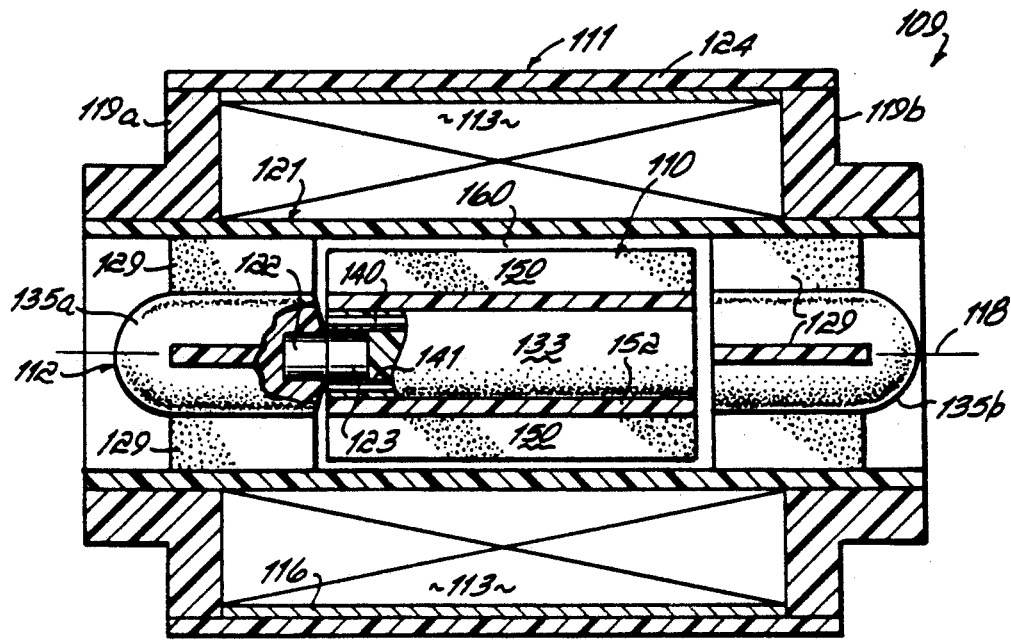
FIG. 6A is a diagrammatic longitudinal cross-sectional view through the center of an axial flow blood pump according to a sixth embodiment of the invention.
Figure 7A:
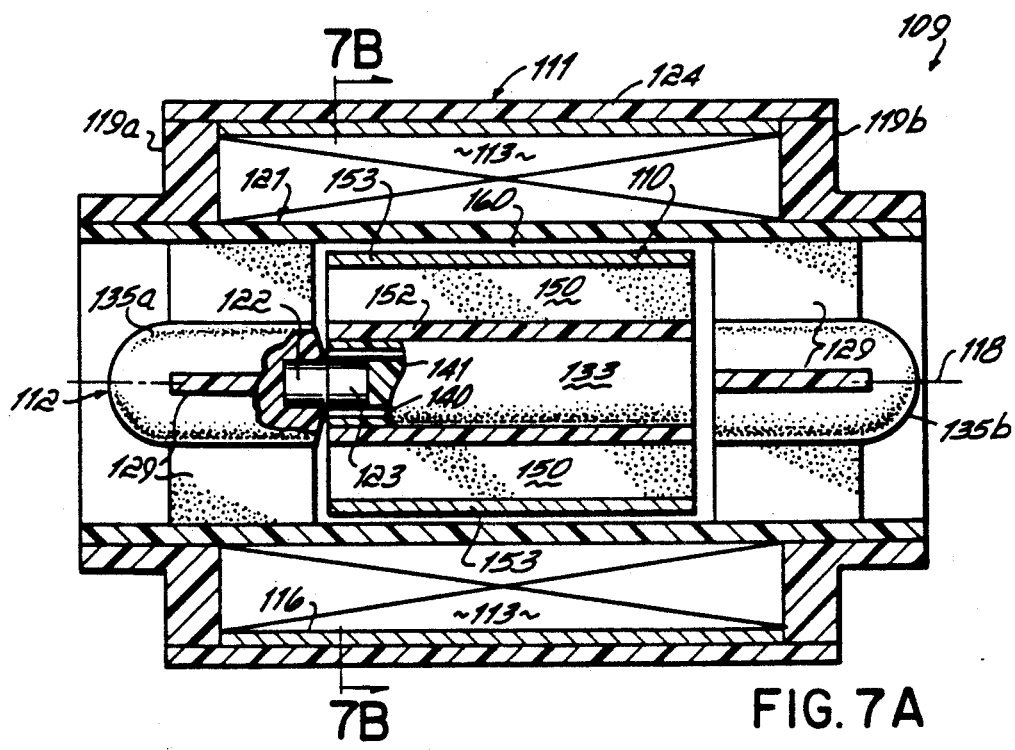
FIG. 7A is a diagrammatic longitudinal cross-sectional view through the center of an axial flow blood pump according to a seventh embodiment of the invention.
Figure 8A:
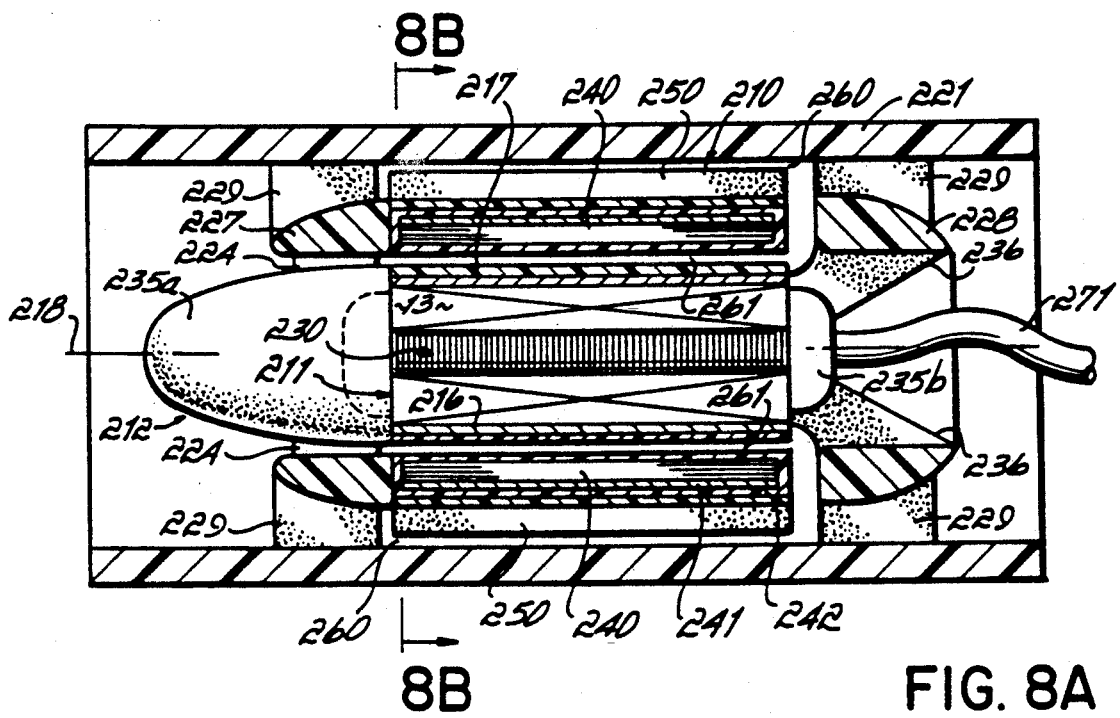
FIG. 8A is a diagrammatic longitudinal cross-sectional view through the center of an axial flow blood pump according to an eighth embodiment of the invention.
Figure 8B:
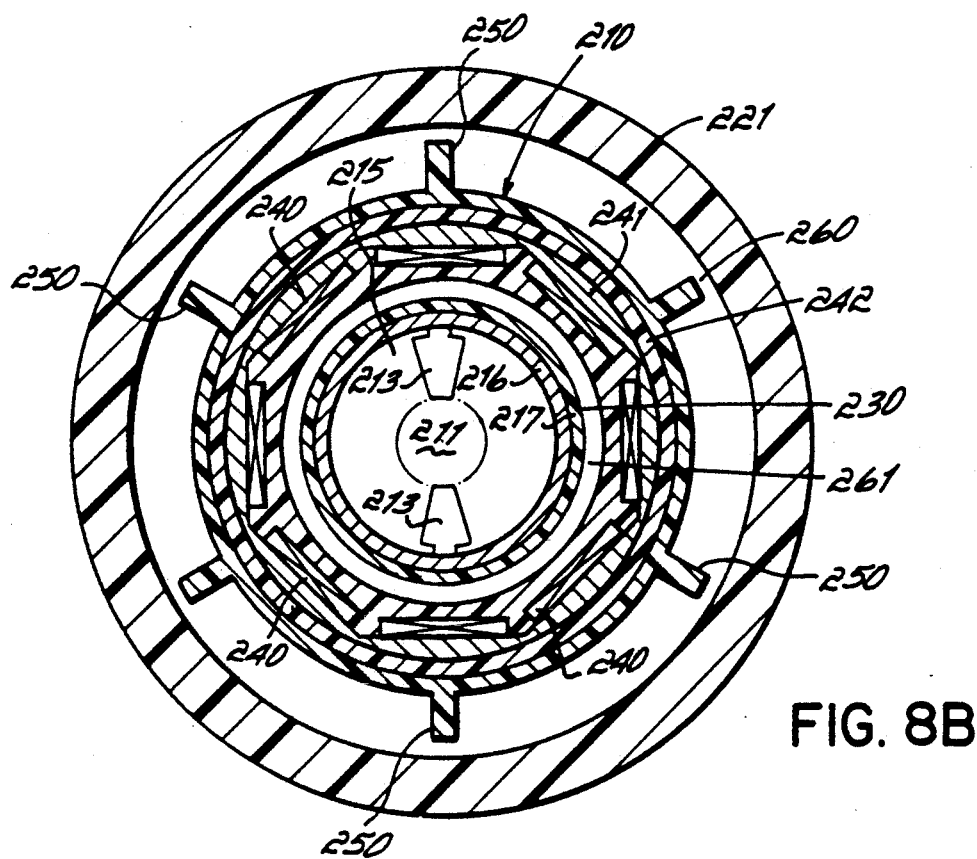
FIG. 8B is a cross-sectional view taken along lines 8B—8B of FIG. 8A.
Figure 9A:
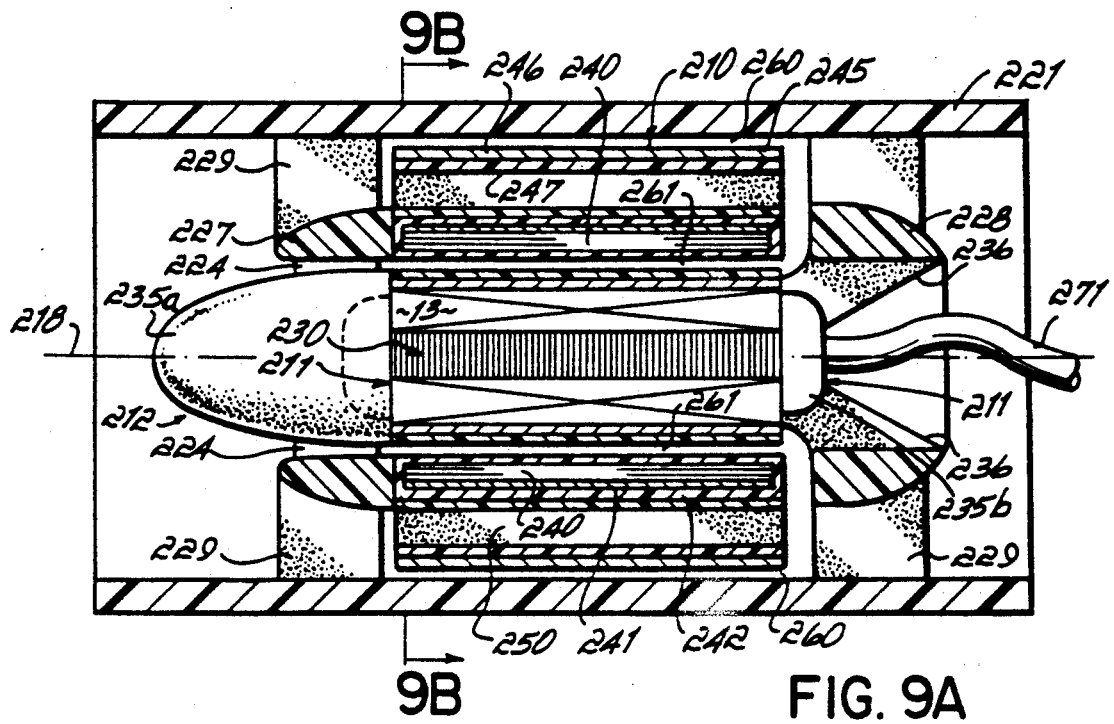
FIG. 9A is a diagrammatic longitudinal cross-sectional view through the center of an axial flow blood pump according to a ninth embodiment of the invention.
Figure 9B:
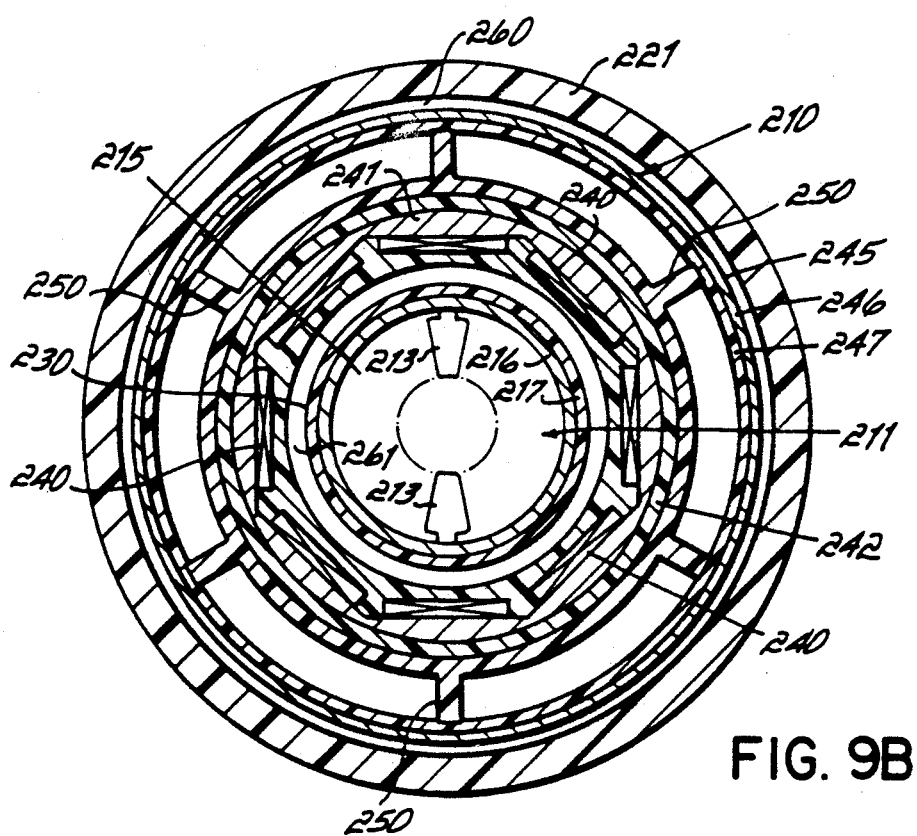
FIG. 9B is a cross-sectional view taken along lines 9B—9B of FIG. 9A.

FIGS. 6A, 7A and 7B show sixth and seventh embodiments of the invention, wherein the rotor 110 has a single stage. Stated in another manner, the midportion 133 has only one set of impeller blades 150 extending radially outwardly therefrom. In both of these single impeller stage embodiments, blood flows through an outer annular gap 160 between the rotor 110 and conduit 121. The gap 160 serves as a single hydrodynamic bearing during rotor 110 rotation. Preferably, gap 160 has a radial dimension of about 0.0035" when the rotor 110 is centered in conduit 121. The outlet end of the rotor 110 preferably has an axial clearance of about 0.003" from outlet pump stator section 135b. The axial clearance dimensions at the inlet end of the rotor 110 are identical to those of the third, fourth and fifth embodiments.

In both the sixth and the seventh embodiments, the radial inner ends of the impeller blades 150 terminate in a hub 152. The sixth embodiment differs from the seventh in that the outer radial ends of the impeller blades 150 are free. Therefore, there is no separation of the blood flow into distinct annular paths. For this reason, it is believed that this embodiment might minimize hemolysis and the possibility of thrombus formation. In a transverse cross sectional view through the thrust bearing, the sixth embodiment is identical to the third embodiment, shown in FIG. 3B.

In the seventh embodiment, the radially outer ends of the impeller blades 150 terminate in a ring 153 which extends the entire axial length of the midportion 133. It is believed that the ring 153 may be better adapted to withstand the wear of extended intracorporeal use in blood, compared to the otherwise unprotected free ends of the impeller blades 150. In transverse cross sectional view through the thrust bearing, the seventh embodiment looks like the third embodiment, except for the addition of ring 153.

As with the first five embodiments, the impeller blades 150 and the stator blades 129 of the sixth and seventh embodiments are preferably angulated. Except for the variations to the rotor 110 and the absence of an intermediate stator 139 in the sixth and seventh embodiments, the other components of the pump 109 are identical to those of embodiments three, four and five.

To assemble the sixth and seventh embodiments, the rotor 110 is axially centered within conduit 121 and then the pump stator 112 components are press fit within inlet and outlet ends of the conduit 121.

VII. The Eighth and Ninth Embodiments

In each of the first seven embodiments of the invention, the motor stator circumscribes the rotor and the housing which defines the blood passageway through the pump. However, as stated in the parent application, it is also contemplated that the motor stator could be located inside the housing, within an axially centered stator hub, and that the magnets, or pole pieces could be mounted within a cylindrical rotor which circumscribes the stator hub.

According to the eighth and ninth embodiments, a motor stator 211 which generates magnetic flux in a conduit 221 is also located within the conduit 221. The pump stator, designated generally by reference numeral 212, and motor stator 211 are circumscribed by a cylindrical rotor 210, which is also located within the conduit 221.

In FIGS. 8A and 8B, and 9A and 9B, reference numerals for component parts have three digits, and the first digit is a "2." The last two digits of the 200 series reference numerals correspond to similarly identified components described with respect to the other embodiments. For instance, the rotor of the first two embodiments is identified by reference numeral 10, by reference numeral 110 in the third, fourth, fifth, sixth and seventh embodiments, and by reference numeral 210 in the eighth and ninth embodiments.

Leads 271 convey electrical signals to the motor stator 211, which is encased within, or integral with, pump stator 212. The leads eventually extend outside of conduit 221 and to a power supply (not shown) and control circuit (not shown), which may also be located intracorporeally.

The pump stator 212 includes an axially centered, elongated hub 230 which houses the motor stator 211. The hub 230 includes inner ring 216 and an outer ring 217. Ring 216 is preferably metal, and ring 217 is preferably plastic. Ring 216 provides rigid structural support, while ring 217 provides a good hydrodynamic bearing surface. The hub 230 has an inlet end 235a and an outlet end 235b. Radial fins 224 extend outwardly from inlet end 235a and connect to a support ring 227. Radial vanes 229 extend further outwardly from ring 227 and are press fit within conduit 221.

Ring 227 serves as an annular thrust bearing during rotation of rotor 210. More particularly, an outlet directed surface of ring 227 coacts with an inlet directed surface of cylindrical rotor 210. The rotor 210 includes a cylinder 242 which encapsulates magnets 240 radially inside a back iron ring 241. A single stage of impeller blades 250 extends radially outwardly from the cylinder 242, thereby defining an outer annular gap 260 between the rotor 210 and conduit 221 and an inner annular gap 261 between the rotor 210 and the pump stator 212 when the rotor 210 is centered in conduit 221. Preferably, gap 260 is about 0.0045", and gap 261 is about 0.0035", though these dimensions could also range from about 0.001" to about 0.010". The axial clearance between the impeller blades 250 and vanes 229 is preferably about 0.003".

Radial fins 236 extend radially outwardly and axially toward the outlet end 235b of hub 230. Outer radial ends of the fins 236 terminate in an outlet support ring 228 which in turn connects to radial vanes 229 that are press fit within conduit 221. Preferably, the axial clearance between ring 228 and the cylinder 242 is about 0.003".

The ninth embodiment differs only from the eighth in that the impeller blades 250 are slightly shorter and their radially outer ends terminate in a rotor support ring 245. The outer gap 260 and inner gap 261 maintain the same radial clearance dimensions as described for the eighth embodiments. The ring 245 actually has a two piece construction, with an outer metal section 246 and an inner plastic section 247. The metal provides strength for the structure and is acceptable for a hydrodynamic bearing surface, so long as conduit 221 is plastic.

In operation, the rotary speed for the rotor 210 for these two single stage/internal motor stator embodiments is preferably about 6000 rpm. This slower speed is due to the greater radial distance of the impeller blades 250 from the axis 218. Faster speeds would probably result in such high impeller blade 250 speeds that the blood would be damaged.

Alternatively, the impeller blades 250 could be located radially inside of the magnets 240. The rotor 210 could then be rotated at a faster speed, and maybe as high as 10,000 rpm.

The eighth and ninth embodiments are best suitable for miniaturization. It is believed that the pump 209 could be manufactured with an outer diameter of 0.275" and an axial length of 0.625", or perhaps even smaller. With these dimensions, the pump 209 could be introduced into the body intravascularly through the femoral artery.

VIII. The Tenth Embodiment

FIGS. 10A and 10B show a hybrid pump 9 which is similar to the first two embodiments and which operates in the same manner. The motor stator 11 is located outside of a conduit 21. The rotor 10 is cylindrical and located axially between inlet section 35a and outlet section 35b of a pump stator 12. An axially elongated stator hub 30 extends through rotor 10. Inlet section 35a includes an annular thrust bearing element 22 which coacts with an annular thrust bearing element 23 molded within an inner ring 51 located radially inside of a single stage of impeller blades 50 of the rotor 10.

The rotor 10 defines outer and inner gaps 60 and 61, respectively, when centered in conduit 21. These gaps preferably have dimensions of 0.0035" and 0.0045", respectively. The single stage of impeller blades 50 is located radially inside of a cylinder 42 which encapsulates magnets 40 and back iron ring 41. At the inlet 25, the axial clearance between the impeller blades 50 and the vanes 29 is also preferably about 0.003". At the outlet 26, the axial clearance between the impeller blades 50 and the vanes 29 is preferably about 0.003".

While the ten embodiments of the invention have been depicted and described in connection with a two-stage pump or a one-stage pump, the principles of the invention may also be embodied in a three-stage pump wherein the rotor carries three stages of impeller blades. Three stages may be necessary to handle large loads.

When used extracorporeally, or external to the body, this axial flow blood pump will be connected to the body just as the connections are made for cardiopulmonary bypass for a heart/lung machine. So this would be the heart of the heart/lung machine. The axial flow blood pump of this invention could also be connected to the femoral artery and femoral vein in the leg. When used in this manner, the axial flow blood pump of this invention can be an assist device for temporary cardiac support. When extremely miniaturized, the pump of this invention can be inserted in the femoral artery for recessitation and/or temporary cardiac support. When the axial flow pump of this invention is implanted with its electronic circuit, expectation for this total artificial heart is that there can be operational capability of up to ten years or more.

To have a rotor that truly floats on blood, hydrodynamically suspended in all axes, the hydrodynamic thrust bearing must work in consort with the radial hydrodynamic bearing to provide long life with minimal hemolysis and minimal potential for thrombus build up.

In short term use for open heart surgery, the utilization of dissimilar rubbing surfaces or like surfaces of hard material represents an adequate solution to an end thrust bearing. However, where necessity calls for low hemolysis and minimal thrombus for life support beyond the open heart operation, or even temporary support, but for rather long term use such as for a total artificial heart, this solution to the end thrust bearing might not be suitable. The hydrodynamic end thrust bearing must allow continuous rapid flow of blood through the gap at the end thrust area to continuously wash the surfaces so as to prevent thrombus build up.

Figure 11:
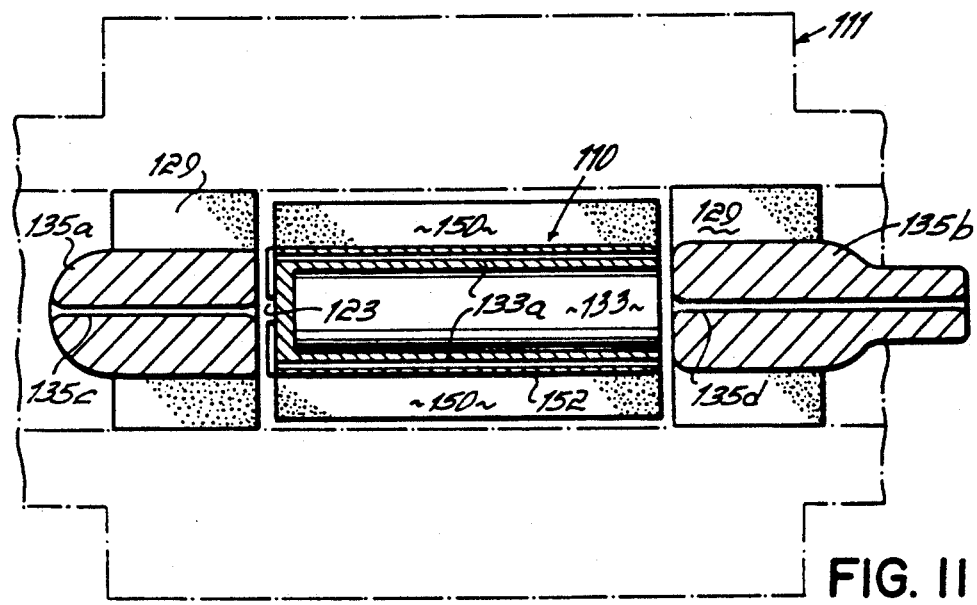
FIG. 11 is a diagrammatic longitudinal cross-sectional view showing a variation of a thrust bearing for the rotor of an axial flow blood pump in accordance with the invention.
Figure 12A:
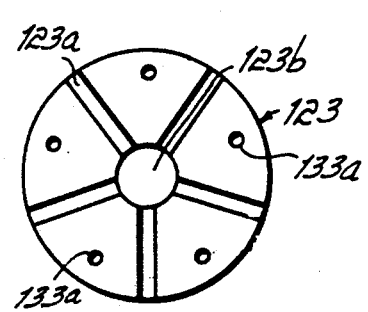
FIG. 12A is an end view of the thrust bearing of the rotor depicted in FIG. 11.
Figure 12B:
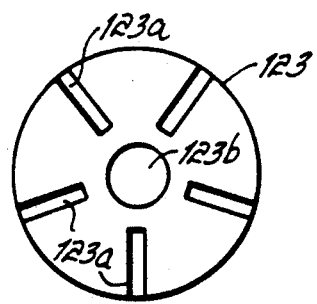
FIGS. 12B–12G show alternative embodiments of the thrust bearing for a rotor of an axial flow blood pump in accordance with the invention.
Figure 12C:
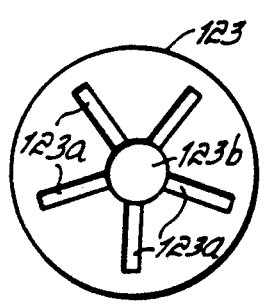
Figure 12D:
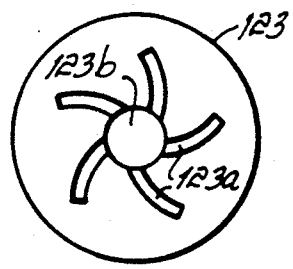
Figure 12E:
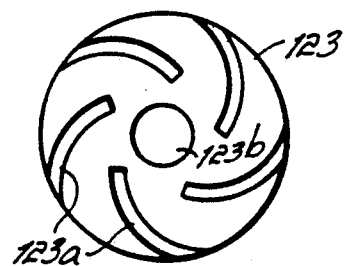
Figure 12F:
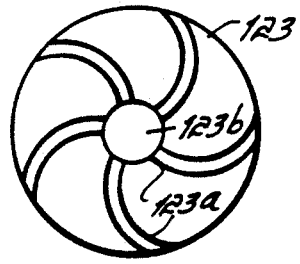
Figure 12G:
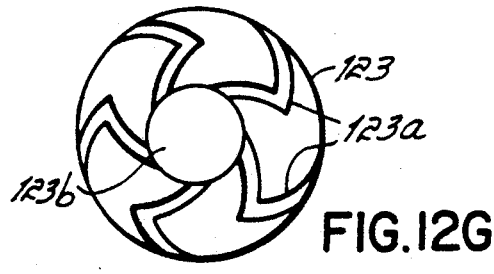
Figure 13A:
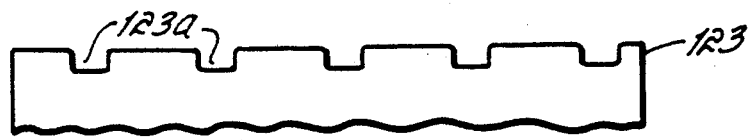
FIG. 13A–13D are circumferential views of four alternatively shaped grooves that may be utilized for the thrust bearing of the rotor of an axial flow blood pump in accordance with the invention.
Figure 13B:
Figure 13C:
Figure 13D:

FIGS. 11-17B show various alternative constructions for the thrust bearing. More specifically, FIG. 11 shows the rotor 110 with an end plate thrust bearing surface 123 which bears on a smooth plate bearing surface 122 of the stator 111. The surface 123 includes grooves 123a and a central depression 123b. The grooves 123a develop a fluid pressure which assists in axially supporting the rotor 110 in a hydrodynamic manner. FIGS. 13A, 13B, 13C and 13D show variations of the cross-sectional shape of the grooves 123a.

FIG. 11 also shows an axial bore 135c through inlet stator section 135a and an axial bore 135d through outlet station section 135b. If desired, the rotor 110 may also have a plurality of axial bores 133a extending longitudinally therethrough. These holes 133a act as an electrostatic bearing, due to blood flow therethrough in the rearward direction.

Figure 14:
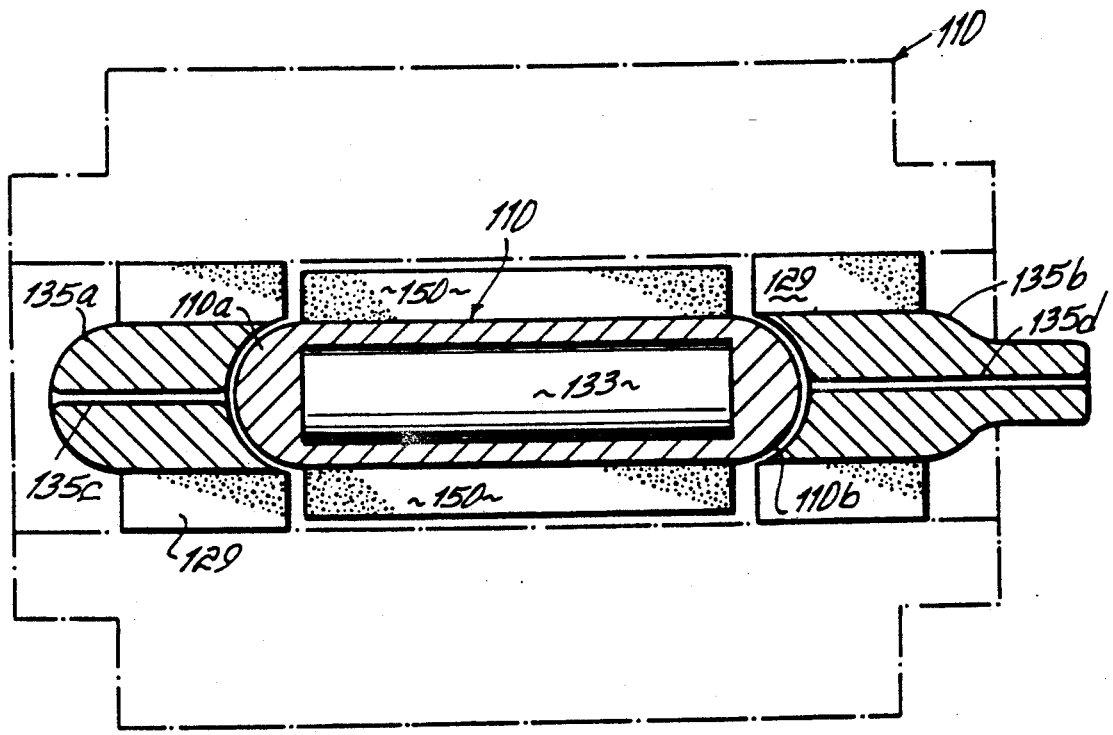
FIG. 14 is a diagrammatic longitudinal cross-sectional view showing a ball-and-socket approach to the rotor of an axial flow blood pump in accordance with the invention.
Figure 15A:
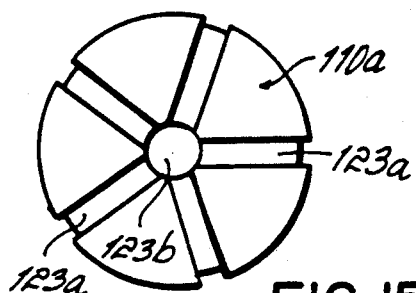
FIG. 15A is a plan view of another alternative approach to thrust bearing design for the rotor depicted in FIG. 14.
Figure 15B:
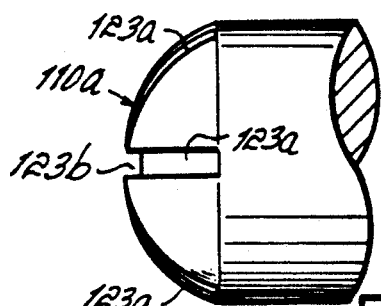
FIG. 15B is a die view of the rotor thrust bearing depicted in FIG. 15A.

FIG. 14 shows a ball-and-socket approach to the axial thrust bearing. In this approach, rotor 110 is rounded at its inlet and outlet ends, as shown by reference numerals 110a and 110b, respectively. Stator inlet and outlet sections, 135a and 135b, respectively, are hollowed to accommodate this rounded shape. According to a further modification of this approach, shown in FIGS. 15A and 15B, the inlet end 110a of the rotor 110 also includes grooves 123a and a central depression 123b.

Figure 16:
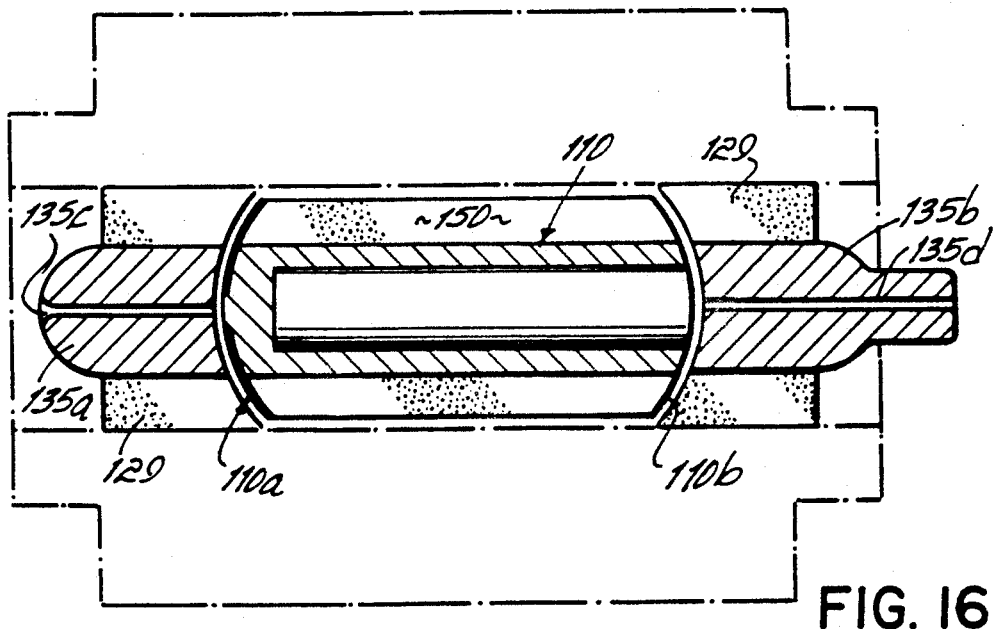
FIG. 16 is a top diagrammatic longitudinal cross-sectional view showing still another variation of the ball-and-socket approach for the rotor of an axial flow blood pump in accordance with the invention.
Figure 17A:
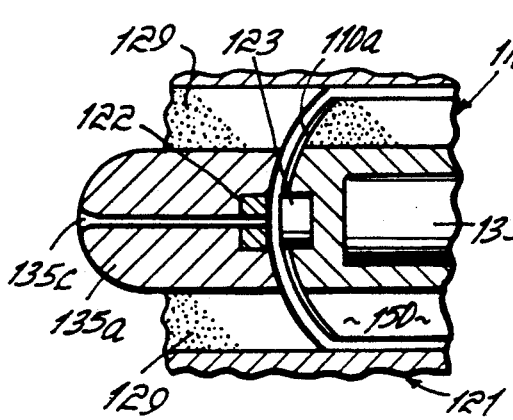
FIGS. 17A and 17B are modifications of the embodiments shown in FIG. 16 and FIG. 14, respectively.
Figure 17B:
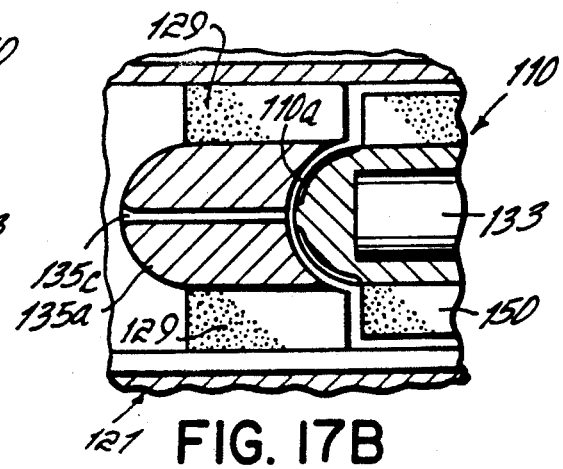

FIG. 16 shows another variation of the ball-and-socket approach, wherein the rotor 110 has rounded inlet and outlet ends, 110a and 110b, respectively, which include rounded impeller blades 150. FIGS. 17A and 17B show further variations of the embodiments shown in FIG. 15 and FIG. 14, respectively.

From the above disclosure of the general principles of the present invention and the preceding detailed description of the preferred embodiment, those skilled in the art will readily comprehend the various modifications to which the present invention is susceptible. For instance, for any of these embodiments, it is possible to rotatably drive the rotor in a manner which would simulate the pulsatile blood flow of a normally functioning human heart. This invention contemplates both continuous blood pumping and pulsatile blood pumping. Moreover, it would be possible to locate the magnets of of pole pieces of the rotor within the impeller blades. Therefore, we desire to be limited only by the scope of the following claims and equivalents thereof:

We claim:

1. An axial flow blood pump for pumping blood through a patient's bloodstream comprising:
    a cylindrical conduit adapted to be disposed in the bloodstream of the patient, the conduit having an internal surface defining a central axial passageway for blood passage therethrough, the passageway having an inner diameter;
    a pump stator mounted within the conduit, the pump stator including axially displaced inlet and outlet sections;
    a cylindrical motor stator located externally of the passageway through the conduit so as to be out of contact with the blood flowing therethrough, the motor stator having windings and a control circuit to create flux in the conduit between the inlet and outlet pump stator sections;
    a rotor axially positioned in the conduit between the inlet and outlet stator sections, the rotor having an outer surface with an outer diameter less than said conduit inner diameter, thereby to define an annular radial gap between the rotor outer surface and the conduit internal surface when the rotor is radially centered in the conduit, the rotor further including,
        a plurality of impeller blades, at least one permanent magnet adapted to interact with said applied flux to rotate the rotor to produce axial blood flow through the passageway from the inlet stator section to the outlet stator section;

whereby, during rotor rotation, the rotor is suspended radially inside the conduit so as to float on the blood and this result is accomplished solely by a hydrodynamic effect created by the presence of said blood flowing within said annular radial gap.

2. The axial flow blood pump of claim 1 wherein said gas has a radial dimension in the range of about 0.001" to 0.010".

3. The axial flow blood pump of claim 1 wherein said rotor includes a single stage of impeller blades.

4. The axial flow blood pump of claim 1 wherein said rotor includes at least two axially spaced sets of impeller blades.

5. The axial flow blood pump of claim 1 and further comprising:

means for controlling the motor stator to rotate the rotor in a manner which produces pulsatile blood flow through the conduit.

6. The axial flow blood pump of claim 1 wherein the impeller blades are of magnetizable material, thereby to facilitate interaction of the rotor with the applied flux to rotate the rotor within the conduit.

7. The axial flow blood pump of claim 1 and further comprising:

a magnet in the pump stator to coact with said at least one magnet carried by the rotor, thereby to serve as a a magnetic thrust bearing for axially and radially centering the rotor within the conduit.

8. The axial flow blood pump of claim 1 wherein said rotor is cylindrical.

9. The axial flow blood pump of claim 8 wherein said impeller blades are located radially inside of said at least one magnet carried by said rotor.

10. The axial flow blood pump of claim 8 wherein said impeller blades are located radially outside of said at least one magnet carried by said rotor.

11. The axial flow blood pump of claim 1 and further comprising:

a rod-shaped, axially centered rotor midportion;
two axially spaced sets of impeller blades extending radially outwardly from said midportion; and
an annular intermediate stator section mounted within the conduit and positioned axially between said spaced sets of impeller blades, the intermediate stator section circumscribing the rotor midportion, said intermediate stator section and said rotor midportion defining an inner annular blood flow gap to serve as an inner hydrodynamic bearing.

12. The axial flow blood pump of claim 11 wherein the intermediate stator section includes a plurality of radially oriented vanes, each of said vanes having an innermost end that terminates in a hub which circumscribes the rotor midportion and an outermost end that terminates at said inner diameter of the conduit, said hub and said rotor midportion defining therebetween said radial inner annular blood flow gap.

13. The axial flow blood pump of claim 11 wherein the intermediate stator section includes a plurality of radially oriented vanes, each of said vanes having an outermost radial end that terminates in a ring which is fixed within the inner diameter of the conduit and an innermost radial end that is radially spaced from the rotor midportion, the innermost radial ends and the rotor midportion defining therebetween said inner annular blood flow gap.

14. The axial flow blood pump of claim 11 wherein a plurality of permanent magnets are mounted within said rotor midportion and extend axially along substantially the entire axial length thereof.

15. The axial flow blood pump of claim 11 wherein said midportion has a reduced radial thickness between said sets of impeller blades.

16. The axial flow blood pump of claim 11 wherein the inlet stator section has a first, outlet directed surface and the rotor midportion has a second, inlet directed surface, said first and second surfaces being of dissimilar materials and cooperatively serving as a thrust bearing to axially support said rotor during blood pumping toward said outlet stator section.

17. The axial flow blood pump of claim 16 wherein one of said first and second surfaces is pointed, thereby to facilitate relative rotatable motion therebetween during blood pumping toward said outlet stator section.

18. The axial flow blood pump of claim 11 wherein the inlet stator section has a first, outlet directed surface and the rotor midportion has a second, inlet directed surface, said first and second surfaces being of identical materials and cooperatively serving as a thrust bearing to axially support said rotor during blood pumping toward said outlet stator section.

19. The axial flow blood pump of claim 18 wherein said first and second surfaces are flat, thereby to facilitate relative rotatable motion therebetween during blood pumping toward said outlet stator section.

20. An axial flow blood pump for pumping blood through a patient's bloodstream comprising:

a cylindrical conduit adapted to be disposed in the bloodstream of the patient, the conduit having an internal surface defining a central axial passageway for blood passage therethrough, the passageway having an inner diameter;
a pump stator mounted within the conduit, the pump stator including axially displaced inlet and outlet sections and a hub extending along the conduit therebetween;
a cylindrical motor stator located externally of the passageway through the conduit so as to be out of contact with the blood flowing therethrough, the motor stator having windings and a control circuit to create flux in the conduit between he inlet and outlet pump stator sections, said motor stator located externally of said conduit;
a cylindrical rotor axially positioned in the conduit between the inlet and outlet stator sections, the cylindrical rotor having an outer surface with an outer diameter less than said conduit inner diameter, thereby to define an outer annular radial gap between said rotor outer surface and said conduit internal surface when the rotor is radially centered in the conduit, the rotor further including,
a plurality of impeller blades extending radially inwardly toward said pump stator hub and defining an inner annular gap therebetween,
at least one permanent magnet located radially outside of said impeller blades and adapted to interact with said applied flux to rotate the rotor to produce axial blood flow through the passageway from the inlet stator section to the outlet stator section;
whereby, during rotor rotation, the rotor is suspended radially inside the conduit so as to float on the blood and this result is achieved solely by hydrodynamic effects created by the presence of said blood flowing through said outer an inner annular gaps, respectively.

21. The axial flow blood pump of claim 20 and further comprising:
   a pair of axially spaced sets of impeller blades; and
   a pair of corresponding, axially spaced impeller support rings, each said set of impeller blades terminating radially internally in one of said support rings, said impeller support rings and said hub defining axially spaced portions of said inner annular gap.

22. The axial flow blood pump of claim 21 wherein said conduit passageway has a central portion with a predetermined length and an increased diameter, said cylindrical rotor located within said central portion and said outer diameter of said rotor being less than said increased diameter and greater than said passageway inner diameter at locations axially beyond said central portion.

23. The axial flow blood pump of claim 21 and further comprising:
   an intermediate set of stator vanes located axially between said axially spaced sets of impeller blades, the radial clearance between said rotor and said stator hub providing an intermediate annular gap.

24. The axial flow blood pump of claim 21 wherein a first of said pair of rotor support rings is located adjacent said pump stator inlet section and further comprising:
   a thrust bearing support ring mounted radially inside of said first impeller support ring, said thrust bearing support ring having an inlet directed surface which coacts with an outlet directed surface of said pump stator inlet section to form an annular thrust bearing for axially supporting said rotor during rotation.

25. The axial flow blood pump of claim 24 wherein said coacting surfaces of said annular thrust bearing are formed of dissimilar materials.

26. The axial flow blood pump of claim 24 wherein said first rotor support ring and said thrust bearing support ring have a plurality of radially oriented throughholes formed therethrough, thereby to permit access for radial blood flow between said thrust bearing support ring and said hub during rotor rotation.

27. An axial flow blood pump for pumping blood through a patient's bloodstream comprising:
   a cylindrical conduit adapted to be disposed in the bloodstream of the patient, the conduit having an internal surface defining a central axial passageway for blood passage therethrough, the passageway having an inner diameter;
   a pump stator mounted within the conduit, the pump stator including axially displaced inlet and outlet sections and a hub extending along the conduit therebetween;
   a motor stator having windings and a control circuit to create flux in the conduit between the inlet and outlet pump stator sections, said motor stator located radially within said pump stator hub and axially between said inlet and outlet sections;
   a cylindrical rotor axially positioned in the conduit between the inlet and outlet stator sections and circumscribing said motor stator, the rotor further including,
   a plurality of impeller blades, the cylindrical rotor having an inner diameter greater than said pump stator and an outer diameter less than said conduit inner diameter, thereby to define an inner annular radial gap between said rotor and said pump stator and an outer annular radial gap between said rotor and said conduit internal surface when the rotor is radially centered in the conduit,
   at least one permanent magnet adapted to interact with said applied flux to rotate the rotor to produce axial blood flow through the passageway from the inlet stator section to the outlet stator section;
   whereby, during rotor rotation, the rotor is suspended radially inside the conduit so as to float on the blood and this result is achieved solely by hydrodynamic effects created by the presence of said blood flowing through said outer an inner annular gaps, respectively.

28. The axial flow blood pump of claim 27 wherein the impeller blades are located radially outside of the magnets.

29. The axial flow blood pump of claim 28 and further comprising:
   a support ring into which outer ends of said impeller blades terminate, the radial clearance between said ring and said conduit internal surface defining said outer annular gap.

30. The axial flow blood pump of claim 27 wherein said rotor includes a single set of impeller blades.

31. The axial flow blood pump of claim 29 wherein said rotor includes a single set of impeller blades.

32. An axial flow blood pump for pumping blood through a patient's bloodstream comprising:
   a cylindrical conduit adapted to be disposed in the bloodstream of the patient, the conduit having an internal surface defining a central axial passageway for blood passage therethrough, the passageway having an inner diameter;
   a pump stator mounted within the conduit, the pump stator including axially displaced inlet and outlet sections;
   a motor stator having windings and a control circuit to create flux in the conduit between the inlet and outlet pump stator sections, said motor stator located outside of said conduit;
   a noncylindrical rotor axially positioned in the conduit between the inlet and outlet stator sections and aligned along a central axis through said conduit, the rotor further including,
   a plurality of impeller blades extending radially outwardly therefrom, the rotor having an outer diameter less than said conduit inner diameter, thereby to define an outer annular radial gap between the rotor and the conduit internal surface when the rotor is radially centered in the conduit,
   at least one permanent magnet located radially inside of said impeller blades and adapted to interact with said applied flux to rotate the rotor to produce axial blood flow through the passageway from the inlet stator section to the outlet stator section;
   whereby, during rotor rotation, the rotor is suspended radially inside the conduit so as to float on the blood and this result is achieved solely by a hydrodynamic effect created by the presence of said blood flowing around said rotor and through said gap.

33. The axial flow blood pump of claim 32 wherein said inlet and said outlet stator sections have an axial bore extending therethrough.

34. The axial flow blood pump of claim 32 wherein the rotor has a plurality of axial bores extending therethrough.

35. The axial flow blood pump of claim 32 and further comprising:
   a rotor midportion;
   two axially spaced sets of impeller blades extending radially outwardly from said rotor midportion;
   an annular, intermediate stator section mounted within the conduit and positioned axially between said axially spaced sets of impeller blades, said intermediate stator section circumscribing said rotor midportion and defining therebetween an inner annular gap which serves as an additional, inner hydrodynamic bearing during rotor rotation.

36. The axial flow blood pump of claim 35 wherein said intermediate stator section includes a plurality of radially oriented vanes, each of said vanes having an innermost end terminating in a hub which circumscribes the rotor midportion and an outermost end terminating at said inner diameter of the conduit, the radial clearance between said hub and said rotor midportion defining said inner annular gap.

37. The axial flow blood pump of claim 35 wherein the intermediate stator section includes a plurality of radially oriented vanes, each of said vanes having an outermost radial end terminating in an outer stator ring fixed within the inner diameter of the conduit and an innermost radial end radially spaced from the rotor midportion, the radial clearance between said innermost radial ends and said rotor midportion defining said inner annular gap.

38. The axial flow blood pump of claim 35 and further comprising:
   a pair of axially spaced impeller blade support rings, each of said impeller blade support rings located at outer radial ends of one of said sets of impeller blades, said outer annular gap defined by the radial clearance between said impeller blade support rings and said conduit internal surface.

39. The axial flow blood pump of claim 37 wherein said impeller blade support rings and said outer stator ring are contoured, thereby to promote blood flow through said conduit with a minimal possibility of blood damage and aggregation.

40. The axial flow blood pump of claim 32 wherein the inlet stator section has a first, outlet directed surface and the rotor midportion has a second, inlet directed surface, said first and second surfaces being of dissimilar materials and cooperatively interacting to serve as a thrust bearing to axially support said rotor during pumping of blood toward said outlet stator section.

41. The axial flow blood pump of claim 40 wherein said dissimilar materials are ceramic and hardened stainless steel.

42. The axial flow blood pump of claim 40 wherein one of said first and second surfaces is ball shaped and the other of said first and second surfaces is socket-shaped, thereby to facilitate relative rotatable motion therebetween during pumping of blood toward said outlet stator section.

43. The axial flow blood pump of claim 40 wherein one of said first and second surfaces is grooved.

44. The axial flow blood pump of claim 40 wherein said dissimilar materials are ceramic and hardened stainless steel and wherein one of the said first and second surfaces is grooved.

* * * * *